(12) United States Patent
Fisher et al.

(10) Patent No.: US 10,166,300 B2
(45) Date of Patent: Jan. 1, 2019

(54) TRIPARTITE CANCER THERANOSTIC NUCLEIC ACID CONSTRUCTS

(71) Applicants: Virginia Commonwealth University, Richmond, VA (US); The Johns Hopkins University, Baltimore, MD (US)

(72) Inventors: Paul B. Fisher, Richmond, VA (US); Swadesh K. Das, Richmond, VA (US); Mitchell E. Menezes, Richmond, VA (US); Devanand Sarkar, Richmond, VA (US); Martin G. Pomper, Baltimore, MD (US)

(73) Assignees: Virginia Commonwealth University, Richmond, VA (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/895,556

(22) PCT Filed: Jun. 4, 2014

(86) PCT No.: PCT/US2014/040912
§ 371 (c)(1),
(2) Date: Dec. 3, 2015

(87) PCT Pub. No.: WO2014/197598
PCT Pub. Date: Dec. 11, 2014

(65) Prior Publication Data
US 2016/0106866 A1 Apr. 21, 2016

Related U.S. Application Data

(60) Provisional application No. 61/830,928, filed on Jun. 4, 2013.

(51) Int. Cl.
| | | |
|---|---|---|
| *A61K 51/00* | (2006.01) | |
| *A61K 9/14* | (2006.01) | |
| *C12N 15/63* | (2006.01) | |
| *C07H 21/04* | (2006.01) | |
| *A61K 48/00* | (2006.01) | |
| *A61K 41/00* | (2006.01) | |
| *A61K 49/00* | (2006.01) | |
| *A61K 51/04* | (2006.01) | |
| *C12Q 1/6897* | (2018.01) | |
| *A61K 9/00* | (2006.01) | |
| *C12N 15/86* | (2006.01) | |
| *A61K 38/20* | (2006.01) | |
| *C12N 7/00* | (2006.01) | |
| *C12N 15/87* | (2006.01) | |
| *A61K 51/12* | (2006.01) | |

(52) U.S. Cl.
CPC ........ *A61K 48/0058* (2013.01); *A61K 9/0019* (2013.01); *A61K 38/20* (2013.01); *A61K 41/0028* (2013.01); *A61K 41/0033* (2013.01); *A61K 49/0013* (2013.01); *A61K 49/0045* (2013.01); *A61K 49/0054* (2013.01); *A61K 51/00* (2013.01); *A61K 51/0491* (2013.01); *C12N 7/00* (2013.01); *C12N 15/86* (2013.01); *C12N 15/87* (2013.01); *C12Q 1/6897* (2013.01); *A61K 51/12* (2013.01); *C07H 21/04* (2013.01); *C12N 2710/10043* (2013.01); *C12N 2710/10343* (2013.01); *C12N 2710/16143* (2013.01); *C12N 2710/16171* (2013.01); *C12N 2830/008* (2013.01)

(58) Field of Classification Search
CPC .... A61K 49/0045; A61K 51/12; C12N 15/86; C12N 2710/10343; C12N 2710/10043; C07H 21/04
USPC ..... 424/1.1, 1.21, 489; 435/320.1; 536/23.5, 536/23.72, 24.1
See application file for complete search history.

(56) References Cited

U.S. PATENT DOCUMENTS

| | | |
|---|---|---|
| 4,405,712 A | 9/1983 | Vande Woude et al. |
| 4,650,764 A | 3/1987 | Temin et al. |
| 5,252,479 A | 10/1993 | Srivastava |
| 6,897,024 B2 | 5/2005 | Bussemakers et al. |
| 7,247,297 B2 | 7/2007 | Weichselbaum et al. |
| 7,321,030 B2 | 1/2008 | Hamada |
| 7,364,727 B2 | 4/2008 | Li et al. |
| 7,816,131 B2 | 10/2010 | Hung et al. |
| 8,034,914 B2 | 10/2011 | Hochberg |
| 2008/0213220 A1 | 9/2008 | Fisher et al. |

(Continued)

FOREIGN PATENT DOCUMENTS

| | | |
|---|---|---|
| WO | WO-89/05345 | 6/1989 |
| WO | WO-90/06997 | 6/1990 |

(Continued)

OTHER PUBLICATIONS

Gao et al., 2013, US 20130281516 A1, effective filing date, Apr. 23, 2010.*

(Continued)

*Primary Examiner* — Shin Lin Chen
(74) *Attorney, Agent, or Firm* — Foley & Lardner LLP

(57) ABSTRACT

The presently disclosed subject matter generally relates to genetic constructs and methods for their use in cancer imaging, cancer treatment, and combined imaging and treatment protocols. In particular, the presently disclosed subject matter relates to tripartite cancer theranostic nucleic acid constructs that permit simultaneous cancer specific viral replication, expression of a diagnostic gene product, and expression of a therapeutic gene.

17 Claims, 10 Drawing Sheets

Specification includes a Sequence Listing.

(56) References Cited

U.S. PATENT DOCUMENTS

| | | | |
|---|---|---|---|
| 2009/0311664 | A1 | 12/2009 | Fong et al. |
| 2011/0176998 | A1 | 7/2011 | Pomper et al. |
| 2011/0313028 | A1 | 12/2011 | Fisher et al. |
| 2012/0195935 | A1 | 8/2012 | Fisher et al. |

FOREIGN PATENT DOCUMENTS

| | | |
|---|---|---|
| WO | WO-92/05266 | 4/1992 |
| WO | WO-92/07573 | 5/1992 |
| WO | WO-92/14829 | 9/1992 |
| WO | WO 2011/017107 A2 * | 2/2011 |
| WO | WO-2012/058522 | 5/2012 |

OTHER PUBLICATIONS

Kosai et al., 2014, US 20140023619 A1, effective filing date, Mar. 25, 2011.*

Nagy et al., 2013, US 20130129635 A1, effective filing date May 24, 2010.*

Fisher et al., 2011, US 20110313028 A1.*

Bhang et al., "Tumor-specific imaging through progression elevated gene-3 promoter-driven gene expression," Nature Medicine, vol. 17, No. 1, Jan. 2011, pp. 123-130.

Das et al., "Cancer Terminator Viruses and Approaches for Enhancing Therapeutic Outcomes," Advances in Cancer Research, vol. 115, 2012, pp. 1-38.

Dash et al., "Inhibition of AP-1 by SARI negatively regulates transformation progression mediated by CCN1," Oncogene 2010, vol. 29, pp. 4412-4423.

Haddad et al., "Molecular imaging of oncolytic viral therapy," Molecular Therapy-Oncolytics, 2015, 8 pages.

Howard et al, "Ultrasound Guided Site Specific Gene Delivery System Using Adenoviral Vectors and Commercial Ultrasound Contrast Agents," Journal of Cellular Physiology, vol. 209, pp. 413-421, 2006.

Search Report issued on EP 14808444.5, dated Dec. 13, 2016.

Watanabe et al, "Advanced two-step transcriptional amplification as a novel method for cancer-specific gene expression and imaging," Oncology Reports, vol. 26, 2011, pp. 769-775.

Berkner. "Development of adenovirus vectors for the expression of heterologous genes," Biotechniques 6: 616-626 (1988).

Blaese et al., "T Lymphocyte-Directed Gene Therapy for ADA-212 SCID: Initial Trial Results After 4 Years," Science 270: 475-479 (1995).

Blasberg et al., "Molecular-genetic imaging: current and future perspectives," J. Clin. Invest. vol. 111; No. 11; pp. 1620-1629; (2003).

Cai et al., "The improved syntheses of 5-substituted 2'-[18F]fluoro-2'-deoxy-arabinofuranosyluracil derivatives ([18F]FAU, [18F]FEAU, [18F]FFAU, [18F]FCAU, [18F]FBAU and [18F]FIAU) using a multistep one-pot strategy," Nuclear Medicine and Biology 38(5): 659-666 (2011).

Chan et al., "Evaluation of F-18-labeled 5-iodocytidine (18 F-FIAC) as a new potential positron emission tomography probe for herpes simplex virus type 1 thymidine kinase imaging," Nuclear Medicine and Biology 38(7): 987-995 (2011).

Chen et al., "Reversal of streptozotocin-induced diabetes in rats by gene therapy with betacellulin and pancreatic duodenal homeobox-1," Gene Ther. 14(14): 1102-1110 (2007).

Cotten et al., "High-efficiency receptor-mediated delivery of small and large (48 kilobase gene constructs using the endosome-disruption activity of defective or chemically inactivated adenovirus particles," Proc. Natl. Acad. Sci. USA 89(13): 6094-6098 (1992).

Danos et al., "Safe and efficient generation of recombinant retroviruses with amphotropic and ecotropic host ranges," Proc. Natl. Acad. Sci. USA 85(17): 6460-6464 (1988).

Dash et al., "Apogossypol derivative BI-97CI (Sabutoclax) targeting Mcl-I sensitizes prostate cancer cells to mda-7/IL-24-mediated toxicity." Proc. Natl. Acad. Sci. USA 108: 8785-8790 (2011).

Dash et al., "Developing an effective gene therapy for prostate cancer: new technologies with potential to translate from the laboratory into the clinic," Discov Med 11: 46-56 (2011).

Donahue et al., "Reduction in SIV replication in rhesus macaques infused with autologous lymphocytes engineered with antiviral genes," Nature Medicine 4(2):181-186 (1998).

Doronin et al., "Tissue-Specific, Tumor-Selective, Replication-Competent Adenovirus Vector for Cancer Gene Therapy," J. Virol. 75(7): 3314-3324 (2001).

Freireich et al., "Quantitative comparison of toxicity of anticancer agents in mouse, rat, hamster, dog, monkey, and man," Cancer Chemother. Rep. 50(4): 219-44 (1966).

Freytag et al., "Phase I Trial of Replication-competent Adenovirus-mediated Suicide Gene Therapy Combined with IMRT for Prostate Cancer," Mol. Ther. 15(5): 10165-1023 (2007).

Fujii et al., "Ultrasound-Targeted Gene Delivery Induces Angiogenesis After a Myocardial Infarction in Mice," J. Am. Coll. Cardiovasc. Imaging 2: 869-879.

Geller et al., "A Defective HSV-1 Vector Expresses *Eschirichia coli* beta-galactosidase in Cultured Peripheral Neurons," Science 241: 1667-1669 (1988).

Gilad et al., "Artificial reporter gene providing MRI contrast based on proton exchange," Nature Biotechnology 25(2): 217-219 (2007).

Gilad et al., "MRI Reporter Genes," J. Nucl. Med. 49(12): 1905-1908 (2008).

Goldman et al., "Lentiviral Vectors for Gene Therapy of Cystic Fibrosis," Human Gene Therapy 10: 2261-2268 (1997).

Graham et al., "Manipulation of Adenovirus Vectors," Methods in Mol. Biol.: Gene Transfer and Expression Protocols 7: 109-127 (1991).

Greco et al., "Eradication of therapy-resistant human prostate tumors using an ultrasound-guided-site-specific cancer terminator virus delivery approach," Mol. Ther. Nov. 3, 2009, vol. 18, pp. 295-306.

Greelish et al., "Stable restoration of the sarcoglycan complex in dystrophic muscle perfused with histamine and a recombinant adeno-associated viral vector," Nature Med. 5:439-443 (1999).

Hallenbeck et al., "A Novel Tumor-Specific Replication-Restricted Adenoviral Vector for Gene Therapy of Hepatocellular Carcinoma," Human Gene Therapy 10(10): 1721-1733 (1999).

Herzog et al., "Long-term correction of canine hemophilia B by gene transfer of blood coagulation factor IX mediated by adeno-associated viral vector," Nature Medicine 5(1): 56-63 (1999).

International Preliminary Report on Patentability for PCT/US2014/040912, dated Dec. 8, 2015.

International Search Report for PCT/US2014/040912,dated Apr. 2, 2015.

Kafri et al., "Sustained expression of genes delivered directly into liver and muscle by lentiviral vectors," Nature Genetics 17(3): 314-317 (1997).

Kishimoto et al., "In vivo imaging of lymph node metastasis with telomerase-specific replication-selective adenovirus," Nature Medicine 12(10): 1312-1219 (2006).

Kurihara et al., "Selectivity of a replication-competent adenovirus for human breast carcinoma cells expressing the MUC1 antigen," J. Clin. Invest. 106: 763-771 (2000).

Lee et al., "Selective Activation of Ceruloplasmin Promoter in Ovarian Tumors: Potential Use for Gene Therapy," Cancer Res. 64(5): 1788 (2004).

Li et al., "Assessment of Recombinant Adenoviral Vectors for Hepatic Gene Therapy," Human Gene Therapy 4:403-409 (1993).

Mocarski et al "Viral Vectors." Gluzman and Hughes (eds.). Cold Spring Harbor Laboratory, Cold Spring Harbor, N.U., 1988, pp. 78-84.

Onodera et al., "Development of Improved Adenosine Deaminase Retroviral Vectors," J. Virol. 72(3):1769-1774 (1998).

Padmanabhan et al., "Visualization of Telomerase Reverse Transcriptase (hTERT) Promoter Activity Using a Trimodality Fusion Reporter Construct," J. Nucl. Med. 47(2): 270-277 (2006).

Piccini et al., "Vaccinia virus as an expression vector," Meth. Enzymology 153: 545-563 (1987).

(56) References Cited

OTHER PUBLICATIONS

Rodriguez et al., "Prostate Attenuated Replication Competent Adenovirus (ARCA) CN706: A Selective Cytotoxic for Prostate-specific Antigen-positive Prostate Cancer Cells," Cancer Res. 57(13): 2559-2563 (1997).
Sambrook et al, "Molecular Cloning. A Laboratory Manual", 2d ed., Cold Spring Harbor Laboratory, New York (1989).
Sarkar et al., "A cancer terminator virus eradicates both primary and distant human melanomas," Cancer Gene Ther. Mar. 7, 2008, vol. 15, pp. 293-302.
Shackleford et al., "Construction of a clonable, infectious, and tumorigenic mouse mammary tumor virus provirus and a derivative genetic vector," Proc. Natl. Acad. Sci. USA 85: 9655-9659 (1988).
Snyder et al., "Correction of hemophilia B in canine and murine models using recombinant adeno-associated viral vectors," Nature Medicine 5(1): 64-70 (1999).
Uhrbom et al., "Dissecting tumor maintenance requirements using bioluminescence imaging of cell proliferation in a mouse glioma model," Nature Medicine 10(11): 1257-1260 (2004).
Venkatesan et., "The potential of celecoxib-loaded hydroxyapatite-chitosan nanocomposite for the treatment of colon cancer," Biomaterials 32(15): 3794-3806 (2011).
Wang et al., "Sustained correction of bleeding disorder in hemophilia B mice by gene therapy," Proc. Natl. Acad. Sci. USA 96: 3906-3910 (1999).
Yaghoubi et al., "Noninvasive detection of therapeutic cytolytic T cells with 18F-FHBG PET in a patient with glioma," Nat. Clin. Pract. Oncol. 6: 53-58 (2009).
Zabner et al., "Safety and efficacy of repetitive adenovirus-mediated transfer of CFTR cDNA to airway epithelia of primates and cotton rats," Nature Genetics 6:75-83 (1994).
Zhang et al., "ABCG2/BCRP Expression Modulates d-Luciferin-Based Bioluminescence Imaging," Cancer Research 67: 9389-9397 (2007).
Communication issued on EP Application 14808444.5 dated Feb. 5, 2018.
Davydova et al., "In vivo bioimaging tracks conditionally replicative adenoviral replication and provides and early indication of viral antitumor efficacy," Cancer Sci, vol. 101, No. 2, Sep. 2009, pp. 474-481.

\* cited by examiner

BLI without covering injected tumor

BLI after covering injected tumor

Injected tumor

Uninjected tumor

```
                             SEQUENCE LISTING

<160> NUMBER OF SEQ ID NOS: 15

<210> SEQ ID NO 1
<211> LENGTH: 40
<212> TYPE: DNA
<213> ORGANISM: Artificial Sequence
<220> FEATURE:
<223> OTHER INFORMATION: PCR primer

<400> SEQUENCE: 1
aaggaaaaaa gcggccgcaa aacaaacaag tacaacatac                              40

<210> SEQ ID NO 2
<211> LENGTH: 35
<212> TYPE: DNA
<213> ORGANISM: Artificial Sequence
<220> FEATURE:
<223> OTHER INFORMATION: PCR primer

<400> SEQUENCE: 2
gtacacgcgt cgacggcgcc ccggagcccg cctttt                                  35

<210> SEQ ID NO 3
<211> LENGTH: 39
<212> TYPE: DNA
<213> ORGANISM: Artificial Sequence
<220> FEATURE:
<223> OTHER INFORMATION: PCR primer

<400> SEQUENCE: 3
gtacacgcgt cgacgccgcc atggaagatg ccaaaaaca                               39

<210> SEQ ID NO 4
<211> LENGTH: 30
<212> TYPE: DNA
<213> ORGANISM: Artificial Sequence
<220> FEATURE:
<223> OTHER INFORMATION: PCR primer

<400> SEQUENCE: 4
atcgcggatc cttacacggc gatcttgccg                                         30

<210> SEQ ID NO 5
<211> LENGTH: 29
<212> TYPE: DNA
<213> ORGANISM: Artificial Sequence
<220> FEATURE:
<223> OTHER INFORMATION: PCR primer

<400> SEQUENCE: 5
atcgcggatc cgagatttcg attccaccg                                          29

<210> SEQ ID NO 6
<211> LENGTH: 27
<212> TYPE: DNA
<213> ORGANISM: Artificial Sequence
<220> FEATURE:
<223> OTHER INFORMATION: PCR primer

<400> SEQUENCE: 6
```

```
ggactagtca ggctttacac tttatgc                                              27

<210> SEQ ID NO 7
<211> LENGTH: 36
<212> TYPE: DNA
<213> ORGANISM: Artificial Sequence
<220> FEATURE:
<223> OTHER INFORMATION: PCR primer

<400> SEQUENCE: 7
aaggaaaaaa gcggccgccg atgtacgggc cagata                                    36

<210> SEQ ID NO 8
<211> LENGTH: 35
<212> TYPE: DNA
<213> ORGANISM: Artificial Sequence
<220> FEATURE:
<223> OTHER INFORMATION: PCR primer

<400> SEQUENCE: 8
gtacacgcgt cgacaatttc gataagccag taagc                                     35

<210> SEQ ID NO 9
<211> LENGTH: 39
<212> TYPE: DNA
<213> ORGANISM: Artificial Sequence
<220> FEATURE:
<223> OTHER INFORMATION: PCR primer

<400> SEQUENCE: 9
gtacacgcgt cgacgccgcc atgaattttc aacagaggc                                 39

<210> SEQ ID NO 10
<211> LENGTH: 30
<212> TYPE: DNA
<213> ORGANISM: Artificial Sequence
<220> FEATURE:
<223> OTHER INFORMATION: PCR primer

<400> SEQUENCE: 10
atcgcggatc ctcagagctt gtagaatttc                                           30

<210> SEQ ID NO 11
<211> LENGTH: 55
<212> TYPE: DNA
<213> ORGANISM: Artificial Sequence
<220> FEATURE:
<223> OTHER INFORMATION: annealing oligonucleotide

<400> SEQUENCE: 11
gatccaataa aatatcttta ttttcattac atctgtgtgt tggttttttg tgtga              55

<210> SEQ ID NO 12
<211> LENGTH: 55
<212> TYPE: DNA
<213> ORGANISM: Artificial Sequence
<220> FEATURE:
<223> OTHER INFORMATION: annealing oligonucleotide

<400> SEQUENCE: 12
ctagtcacac aaaaaaccaa cacacagatg taatgaaaat aaagatattt tattg              55

<210> SEQ ID NO 13
<211> LENGTH: 36
<212> TYPE: DNA
<213> ORGANISM: Artificial Sequence
```

```
<220> FEATURE:
<223> OTHER INFORMATION: PCR primer

<400> SEQUENCE: 13
gtacacgcgt cgacgccgcc atgcccacgc tactgc                              36

<210> SEQ ID NO 14
<211> LENGTH: 29
<212> TYPE: DNA
<213> ORGANISM: Artificial Sequence
<220> FEATURE:
<223> OTHER INFORMATION: PCR primer

<400> SEQUENCE: 14
atcgcggatc ctcagttagc ctcccccat                                       29

<210> SEQ ID NO 15
<211> LENGTH: 838
<212> TYPE: DNA
<213> ORGANISM: Artificial Sequence
<220> FEATURE:
<223> OTHER INFORMATION: Promoter sequence

<400> SEQUENCE: 15
tccaaaaaca aacaagtaca acatacccaa aagagggaag ggctggagga gtgggggaga     60
cctctgcctg ggaatttgcc agacgatggg caagtttccc cccgccccac ccccccccc    120 gccttttcat tcataaatgc cactgtgggt attaatttgc aattcactga actttgctaa   180
taaacatcat gccaaagctt tgggacttgt tccgaacacg cctctttgaa gtccacaaat   240
attcctgact cagagacaca ctcctcttcc ccgttctact ctttcaacag ataacttgcc   300
tctcaccttc gctgtaaaaa agcaaacagc tcactgcctt cccgggtgag ggcttcagtg   360 gctgccggt  caactcgcat caccaaacaa aacgacttt  gttcctccct ctcaggtcct   420
cccacccacc cagtccaggc aaagttctga actggccccc tcgcccctca cgaccctcca   480
actaccatca ccaccatcac gccccaaaga acccttccca acataagtcg taatttaagg   540
tggaaaaaac gaactgtttt cttgacgggt ctgggacaca cacacacaca cacacacaca   600
cacacaccga actgttttct tgacgggtct gggagacaca cacacacaca cacacacaca   660
cacacacaca cacacacaca caaaggtgca atggggccag gggaggcgct tggcagcagc   720
ccgcgccaac cagcattcct gagatgtttg agaattctgg aacgcgcaga cagagccgac   780
gtcactgcaa cacgcggcgc ctccgccggc ccgtataaaa ggcgggctcc ggggcgcc    838
```

TRIPARTITE CANCER THERANOSTIC NUCLEIC ACID CONSTRUCTS

CROSS-REFERENCE TO RELATED APPLICATIONS

This application is a U.S. national stage application under 35 U.S.C. § 371 of International Application No. PCT/US2014/040912, filed Jun. 4, 2014, which claims the benefit of U.S. Provisional Application No. 61/830,298, filed Jun. 4, 2013, which are incorporated herein by reference in their entireties.

FIELD OF THE INVENTION

The presently disclosed subject matter generally relates to genetic constructs and methods for their use in cancer imaging, cancer treatment, and combined imaging and treatment protocols. In particular, the presently disclosed subject matter relates to tripartite cancer theranostic nucleic acid constructs that permit simultaneous cancer-specific viral replication, expression of a diagnostic gene product, and expression of a therapeutic gene.

BACKGROUND

Targeted imaging of cancer remains an important but elusive goal. Such imaging could provide early diagnosis, detection of metastasis, aid treatment planning and benefit therapeutic monitoring. By leveraging the expanding list of specific molecular characteristics of tumors and their microenvironment, molecular imaging also has the potential to generate tumor-specific reagents. But many efforts at tumor-specific imaging are fraught by nonspecific localization of the putative targeted agents, eliciting unacceptably high background noise.

While investigators use many strategies to provide tumor-specific imaging agents—largely in the service of maintaining high target-to-background ratios—they fall into two general categories, namely direct and indirect methods (Blasberg & Tjuvajev (2003) *J. Clin. Invest.* 111:1620-1629). Direct methods employ an agent that reports directly on a specific parameter, such as a receptor, transporter or enzyme concentration, usually by binding directly to the target protein. Indirect methods use a reporter transgene strategy, in analogy to the use of green fluorescent protein (GFP) in vitro, to provide a read-out on cellular processes occurring in vivo by use of an external imaging device. Molecular-genetic imaging employs an indirect technique that has enabled the visualization and quantification of the activity of a variety of gene promoters, transcription factors and key enzymes involved in disease processes and therapeutics in vivo including Gli (Zhang (2007) *Cancer Res.* 67:9389-9397), E2F1 (Uhrbom et al. (2004) *Nat. Med.* 10:1257-1260), telomerase (Kishimoto et al. (2006) *Nat. Med.* 12:1213-1219; Padmanabhan et al. (2006) *J. Nucl. Med.* 47:270-277), and several kinases, including one that has proved useful in human gene therapy trials (Freytag et al. (2007) *Mol. Ther.* 15:1016-1023; Yaghoubi et al. (2009) *Nat. Clin. Pract. Oncol.* 6:53-58). Unfortunately, these techniques have been limited by problems relating to insufficient specific localization of imaging agents and unacceptably high background noise.

The presently disclosed subject matter relates to tripartite cancer theranostic nucleic acid constructs. Such nucleic acid constructs permit simultaneous cancer-specific viral replication, expression of a diagnostic gene product, and expression of a therapeutic gene.

SUMMARY

The presently disclosed subject matter provides a tripartite nucleic acid construct comprising a first promoter operably linked to at least one gene required for viral replication, a second promoter operably linked to a gene encoding an imaging agent, and a third promoter operably linked to a gene encoding a therapeutic agent, wherein the first promoter and the second promoter are each cancer-selective. In some aspects, the nucleic acid construct is selected from the group consisting of adenoviral, lentiviral, retroviral, adeno-associated viral, and herpes simplex viral. In one aspect, the first promoter is PEG-Prom (Progression elevated gene-3 promoter). In another aspect, at least one gene required for viral replication is adenovirus early region 1A (E1A) or early region 1B (E1B). In a further aspect, the second promoter is CCN1 (cysteine-rich, angiogenic inducer 61/CYR61) or a truncated version thereof. In still further aspects, the imaging agent is selected from the group consisting of β-galactosidase, luciferase, horse radish peroxidase, thymidine kinase, and alkaline phosphatase. In yet another aspect, the imaging agent is herpes simplex virus thymidine kinase (HSV-tk). In another aspect, the third promoter is a constitutive promoter, particularly wherein the third promoter is cytomegalovirus (CMV). In a further aspect, the third promoter is a cancer-selective promoter. In a still further aspect, the therapeutic agent is selected from the group consisting of an anti-cancer agent, an apoptosis inducing agent, a tumor suppressor agent, an immune system enhancing agent, and an immunomodulatory agent, particularly wherein the therapeutic agent is an immunomodulatory cytokine, and more particularly wherein the immunomodulatory cytokine is mda-7/IL-24 or a truncated variant thereof such as M4. In yet another aspect, cells, particularly cancer cells, comprising the tripartite nucleic acid construct are also provided.

In another aspect of the presently disclosed subject matter, a method of imaging and treating cancerous cells in a subject is provided, comprising the steps of: a) administering to the subject a tripartite nucleic acid construct comprising a first promoter operably linked to at least one gene required for viral replication, a second promoter operably linked to a gene encoding an imaging agent, and a third promoter operably linked to a gene encoding a therapeutic agent, wherein the first promoter and the second promoter are each cancer-selective; and b) imaging cancerous cells in the subject by detecting a detectable signal from the imaging agent, wherein the gene encoding the therapeutic agent is expressed in the cancerous cells. In some aspects, the step of imaging is carried out via single photon emission computed tomography (SPECT) or by positron emission tomography (PET) or by bioluminescent imaging (BLI). In another aspect, the step of administering the nucleic acid construct is carried out by intravenous injection. In a further aspect, the cancerous cells are selected from the group consisting of breast cancer, melanoma, carcinoma of unknown primary (CUP), neuroblastoma, malignant glioma, cervical, colon, hepatocarcinoma, ovarian, lung, pancreatic, and prostate cancer. In some aspects, the nucleic acid construct is selected from the group consisting of adenoviral, lentiviral, retroviral, adeno-associated viral, and herpes simplex viral. In one aspect, the first promoter is PEG-Prom. In another aspect, at least one gene required for viral replication is adenovirus early region 1A (E1A) or early region 1B (E1B). In a further aspect, the second promoter is CCN1 or a truncated version thereof. In still further aspects, the imaging agent is selected from the group consisting of β-galactosidase, luciferase, horse radish peroxidase, thymidine kinase, and alkaline phosphatase. In yet another aspect, the imaging agent is herpes simplex virus thymidine kinase (HSV-tk). In another aspect, the third promoter is a constitutive promoter, particularly wherein the third promoter is cytomegalovirus (CMV). In a further aspect, the third promoter is a cancer-selective promoter. In a still further aspect, the therapeutic agent is selected from the group consisting of an anti-cancer agent, an apoptosis inducing agent, a tumor suppressor agent, an immune system enhancing agent, and an immunomodulatory agent, particularly wherein the therapeutic agent is an immunomodulatory cytokine, and more particularly wherein the immunomodulatory cytokine is mda-7/IL-24 or a truncated variant thereof such as M4.

In another aspect of the presently disclosed subject matter, a composition comprising an ultrasound targeted microbubble population is provided, wherein the microbubble population stably binds a tripartite nucleic acid construct, and wherein the tripartite nucleic acid construct comprises a first promoter operably linked to at least one gene required for viral replication, a second promoter operably linked to a gene encoding an imaging agent, and a third promoter operably linked to a gene encoding a therapeutic agent, wherein the first promoter and the second promoter are each cancer-selective.

In a further aspect, a method for delivering a tripartite nucleic acid construct to cancerous cells in a subject is provided, comprising the steps of: a) providing an ultrasound targeted microbubble population stably binding the tripartite nucleic acid construct; b) providing an ultrasound device capable of directing the microbubble population to the cancer cells; c) directing the microbubble population to the cancer cells with the ultrasound device; and d) bursting the microbubble population under conditions such that the tripartite nucleic acid construct is delivered to the cancer cells; wherein the tripartite nucleic acid construct comprises a first promoter operably linked to at least one gene required for viral replication, a second promoter operably linked to a gene encoding an imaging agent, and a third promoter operably linked to a gene encoding a therapeutic agent, wherein the first promoter and the second promoter are each cancer-selective.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
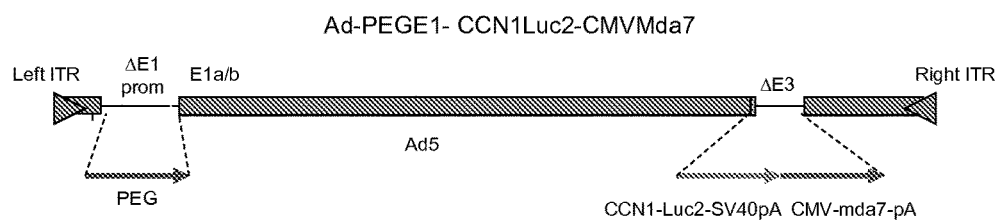
Figure 2:
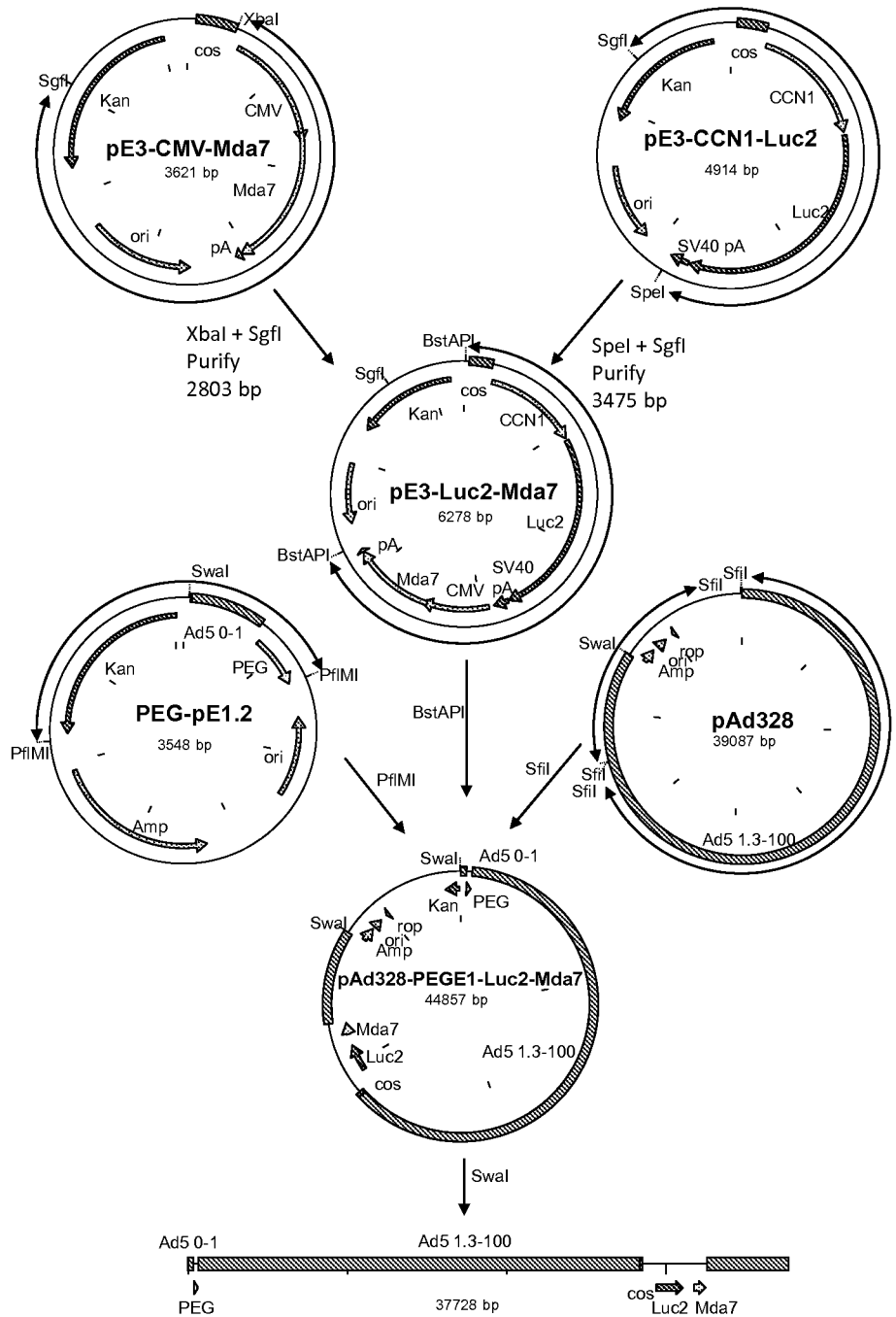
Figure 3:
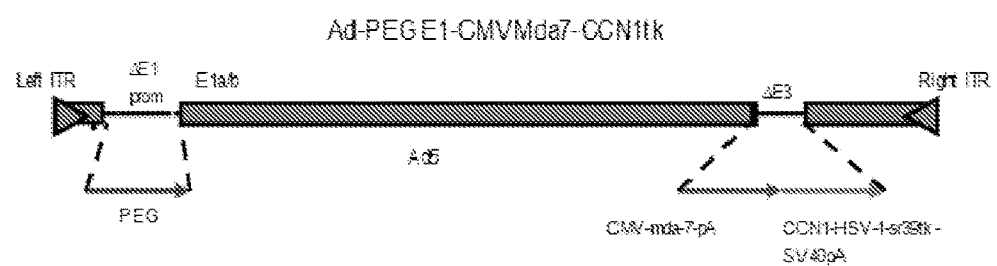
Figure 4:
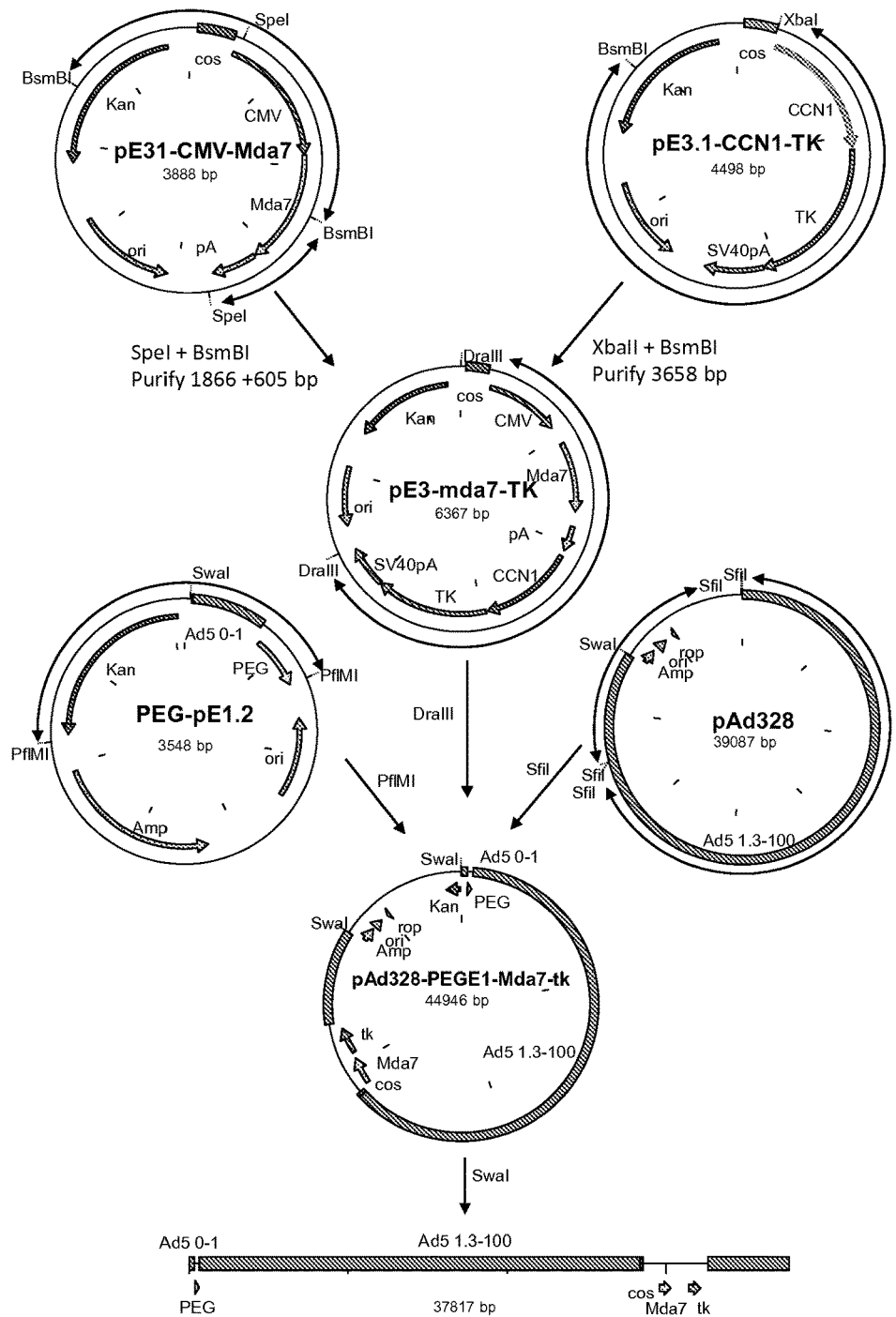
Figure 5A:
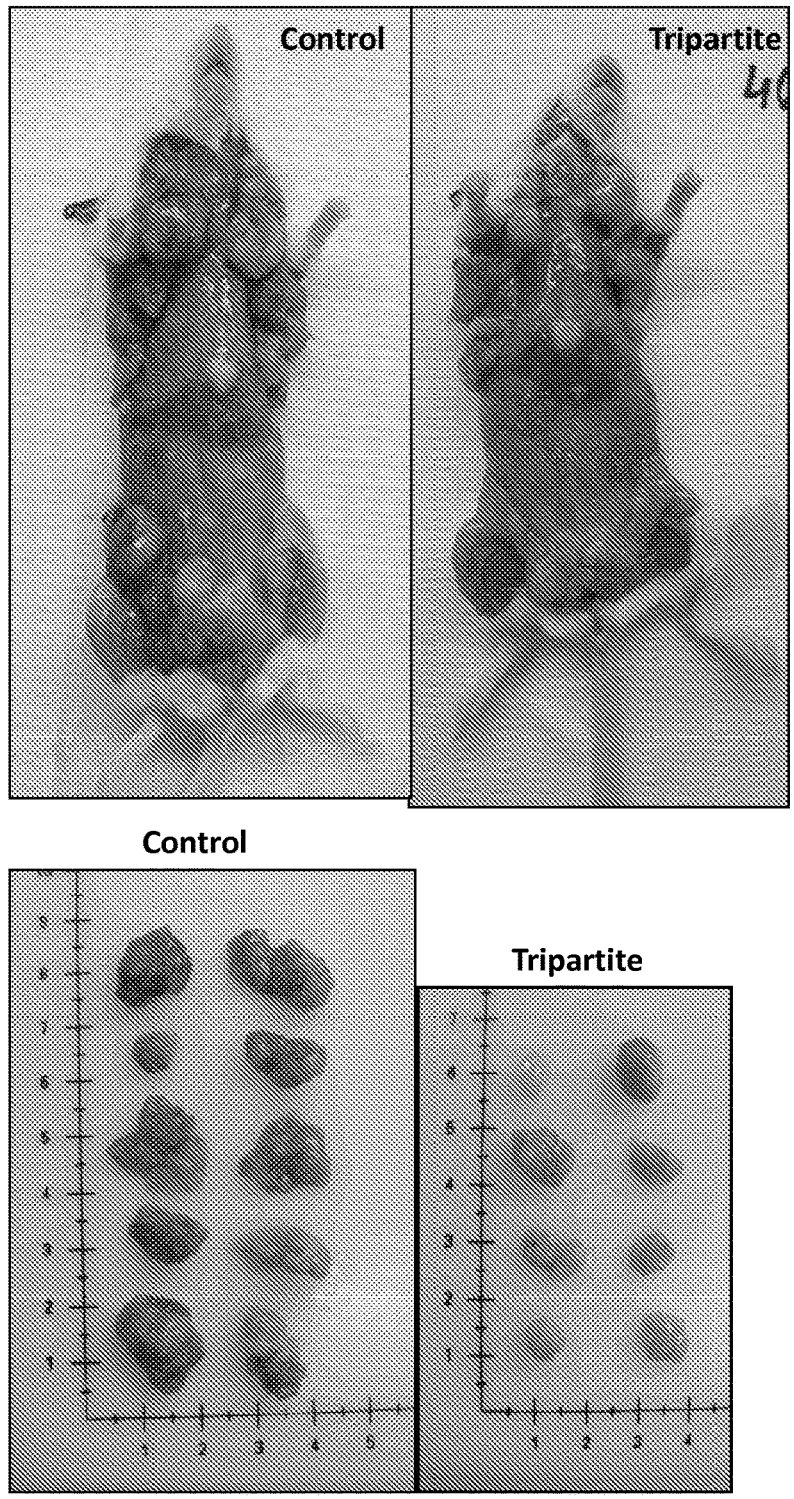
Figure 5B:
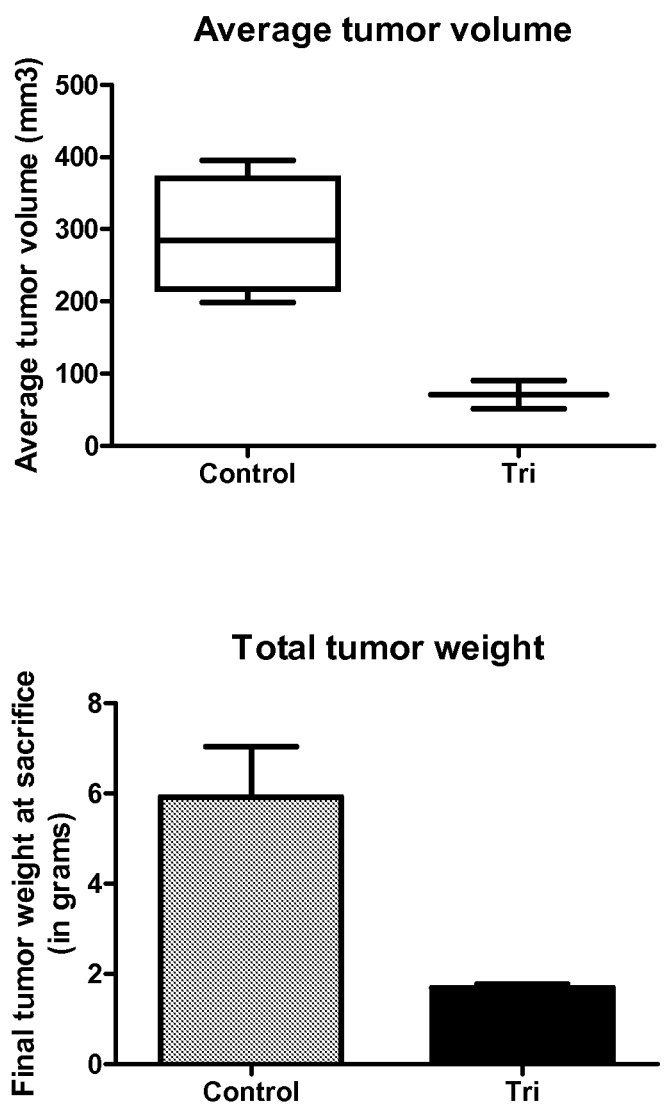
Figure 6A:
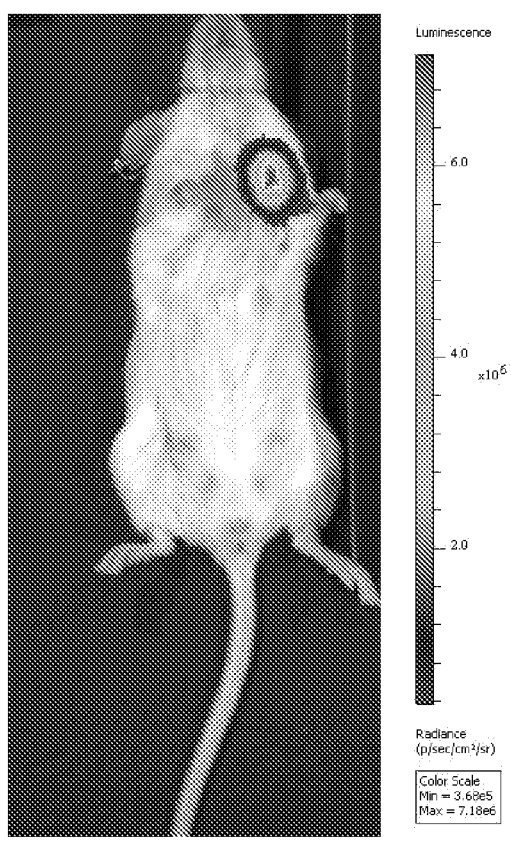
Figure 6B:
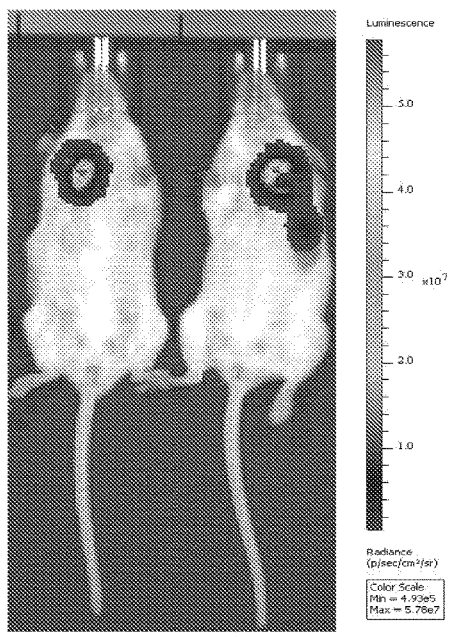
Figure 6B:
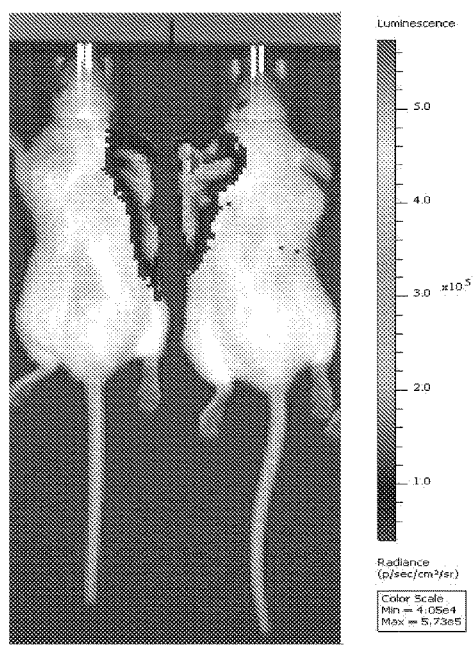

Having thus described the presently disclosed subject matter in general terms, reference will now be made to the accompanying Figures, which are not necessarily drawn to scale, and wherein:

FIG. 1 shows a schematic diagram of a conditionally-replicative adenovirus vector containing the E1A/B (E1A/E1B) region under the control of a PEG promoter and two expression cassettes in the E3 region (CCN1-Luc2 and CMV-mda-7);

FIG. 2 shows a schematic diagram of a shuttle plasmid for inserting two expression cassettes in tandem into the E3 region of a viral vector using plasmids pE3.1-CMV-mda-7 and pE3.1-CCN1-Luc. Specifically, the 2803 bp XbaI-SgfI fragment from pE3-CMV-mda-7 was ligated with the 3475 bp SpeI-SgfI fragment from pE3-CCN1-Luc2, generating plasmid pE3-Luc2-mda-7;

FIG. 3 shows a schematic diagram of a conditionally-replicative adenovirus vector containing the E1A/B (E1A/E1B) region under the control of a PEG promoter and two expression cassettes in the E3 region (CCN1-HSV and CMV-mda-7);

FIG. 4 shows a schematic diagram of a shuttle plasmid for inserting two expression cassettes in tandem into the E3 region of a viral vector using plasmids pE3.1-CMV-mda-7 and pE3.1-CCN1-tk. Specifically, the 1866 bp BsmBI fragment and the 605 bp BsmBI-SpeI fragment from pE3.1-CMV-Mda7 was ligated with the 3658 bp XbaI-BsmBI fragment from pE3.1-CCN1-tk, generating plasmid pE3-mda-7-tk;

FIG. 5A shows representative images of mice and tumors from control mice and tripartite virus (Ad.PEG-E1A-CCN1-Luc2-CMV-mda-7/TCTV-Luc7) treated mice at sacrifice. FIG. 5B shows tumor volumes and tumor weights of control and tripartite virus treated mice at sacrifice;

FIG. 6 shows bioluminescent imaging results of mice following treatment of a single (A) or multiple tumors (B) with the tripartite virus (Ad.PEG-E1A-CCN1-Luc2-CMV-mda-7/TCTV-Luc7); and FIG. 7 shows that uninjected tumors can also be visualized following injection of a single tumor with the tripartite virus (Ad.PEG-E1A-CCN1-Luc2-CMV-mda-7/TCTV-Luc7) virus both in the intact mouse (A) and in the tumors (B).

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Progress in systemic cancer virotherapy has previously been hampered for several reasons that include: 1) trapping of viruses in the liver; 2) clearance of viruses by the immune system; and 3) lack of true cancer-specific expression of transgenes. In addition, when using adenoviruses, the lack of sufficient Coxsackie Adenovirus Receptors (CAR) to permit viral entry into certain cancer cells has also proven problematic. The presently disclosed subject matter overcomes these problems through the use of a nucleic acid construct with a high level of specificity for target cancer cells in order to simultaneously visualize and destroy tumors and metastases (i.e., "theranostics").

The nucleic acid constructs of the presently disclosed subject matter are unique and novel in that they contain three different promoters driving different genes, two of the promoters being cancer-specific promoters and the third being a constitutive promoter, with unique cancer specificity. In particular, two Tripartite Cancer Theranostic Vectors (TCTVs) were produced and characterized. One nucleic acid construct was a tripartite cancer theranostic adenoviral vector (Ad.PEG-E1A-CCN1-Luc2-CMV-mda-7) (TCTV-Luc7) comprising: 1) a PEG-Prom promoter controlling expression of E1A and E1B for cancer cell-specific replication; 2) a cancer-specific CCN1-Prom promoter controlling expression of the luciferase gene; and 3) a constitutive CMV-Prom promoter controlling expression of the mda-7/IL-24 gene. Another nucleic acid construct was a tripartite cancer theranostic adenoviral vector (Ad.PEG-E1A-CMV-mda-7-CCN1-tk) (TCTV-Tk7) comprising: 1) a PEG-Prom promoter controlling expression of E1A and E1B for cancer cell-specific replication; 2) a cancer-specific CCN1-Prom promoter controlling expression of the HSV-tk gene; and 3) a constitutive CMV-Prom promoter controlling expression of the mda-7/IL-24 gene. A tripartite nucleic acid construct may also be designed that employs three cancer-restricted promoters for even more tightly regulated gene expression (e.g., for delivery of a non-cancer specific toxic gene product to cancer cells). Similar nucleic acid constructs may be generated using a variety of viral systems, including adenovirus or lentivirus, vaccinia virus, and the like, as well as TCTV producing other therapeutic genes (e.g., TRAIL, Survivin, wt p53, and the like), a novel surface antigen making cancer cells more immunogenic (e.g., HLA, HLA-B7, foreign antigen, and the like) or a chaperone protein enhancing the immune system to produce a vaccine effect (e.g., grp170, HSP, and the like) (to produce a vaccine effect).

The presently disclosed subject matter has wide applicability for the diagnosis and therapy of cancer. For example, the TCTV-tk7 vector may be used in humans to visualize tumors using positron emission tomography (PET), single photon emission computed tomography (SPECT), magnetic resonance imaging (MRI) and optical imaging. In addition, by modifying the tropism of the adenovirus (e.g., the Ad.5/3 modification), and through use of ultrasound targeted microbubble destruction (UTMD), such vectors may be delivered for diagnostics/therapy in defined regions of the body where metastatic cells may reside.

I. Genetic Constructs

The presently disclosed subject matter provides a tripartite nucleic acid construct comprising a first promoter operably linked to at least one gene required for viral replication, a second promoter operably linked to a gene encoding an imaging agent, and a third promoter operably linked to a gene encoding a therapeutic agent, wherein the first promoter and the second promoter are each cancer-selective. In one aspect, the first promoter is PEG-Prom. In another aspect, the at least one gene required for viral replication is adenovirus early region 1A (E1A) or early region 1B (E1B). In a further aspect, the second promoter is CCN1 or a truncated version thereof (see, e.g., SEQ ID NO:15). In still further aspects, the imaging agent is selected from the group consisting of β-galactosidase, luciferase, horseradish peroxidase, thymidine kinase, and alkaline phosphatase. In yet another aspect, the imaging agent is herpes simplex virus thymidine kinase (HSV-tk).

A variety of methods and systems for DNA delivery are known in the art and may be used within the compositions and methods of the presently disclosed subject matter, including without limitation lipid-based systems (e.g., cationic lipids, lipoplexes, lipid-modified polycations, emulsions, and high density lipoprotein (HDL)); organic nanoparticles (e.g., polyplexes, micelles (block and graft copolymers), and nanogels); inorganic nanoparticles (e.g., calcium phosphate particles, super paramagnetic iron oxide nanoparticles (SPIONs) and nanodiamonds); and natural vesicles (e.g., virus like particles (VLPs) and exosomes).

Vectors which comprise the nucleic acid constructs described herein are also encompassed by embodiments of the invention and include both viral and non-viral vectors. As used herein, the term "vector" refers to a nucleic acid construct designed for transduction/transfection of one or more cell types. Vectors may be, for example, "cloning vectors," which are designed for isolation, propagation and replication of inserted nucleotides, "expression vectors," which are designed for expression of a nucleotide sequence in a host cell, a "viral vector," which is designed to result in the production of a recombinant virus or virus-like particle, or "shuttle vectors," which comprise the attributes of more than one type of vector. The term "replication" means duplication of a vector.

The term "expression vector" is used interchangeably herein with the term "plasmid" and "vector" and refers to a recombinant DNA molecule containing a desired coding sequence and appropriate nucleic acid sequences necessary for expression of the operably linked coding sequence (e.g., an insert sequence that codes for a product) in a particular host cell. The term "plasmid" refers to an extrachromosomal circular DNA capable of autonomous replication in a given cell. In certain embodiments, the plasmid is designed for amplification and expression in bacteria. Plasmids can be engineered by standard molecular biology techniques. See Sambrook et al., Laboratory Manual, Cold Spring Harbor Laboratory Press, Cold Spring Harbor (1989), N.Y. Nucleic acid sequences necessary for expression in prokaryotes usually include a promoter, an operator (optional), and a ribosome binding site, often along with other sequences.

Exemplary viral vectors include but are not limited to: bacteriophages, various baculoviruses, retroviruses, and the like. Those of skill in the art are familiar with viral vectors that are used in gene therapy applications, which include but are not limited to: Herpes simplex virus vectors (Geller et al. (1988) *Science* 241:1667-1669); vaccinia virus vectors (Piccini et al. (1987) *Meth. Enzymology*, 153:545-563); cytomegalovirus vectors (Mocarski et al., in Viral Vectors, Y. Gluzman and S. H. Hughes, Eds., Cold Spring Harbor Laboratory, Cold Spring Harbor, N. Y., 1988, pp. 78-84)); Moloney murine leukemia virus vectors (Danos et al. (1988) *Proc. Natl. Acad. Sci. USA* 85:6460-6464; Blaese et al. (1995) *Science* 270:475-479; Onodera et al. (1988) *J. Virol.* 72:1769-1774; adenovirus vectors (Berkner (1988) *Biotechniques* 6:616-626; Cotten et al. (1992) *Proc. Natl. Acad. Sci. USA* 89:6094-6098; Graham et al. (1991) *Meth. Mol. Biol.* 7:109-127; Li et al. (1993) *Human Gene Therapy* 4:403-409; Zabner et al. (1994) *Nature Genetics* 6:75-83); adeno-associated virus vectors (Goldman et al. (1997) *Human Gene Therapy* 10:2261-2268; Greelish et al. (1999) *Nature Med.* 5:439-443; Wang et al. (1999) *Proc. Natl. Acad. Sci. USA* 96:3906-3910; Snyder et al. (1999) *Nature Med.* 5:64-70; Herzog et al. (1999) *Nature Med.* 5:56-63); retrovirus vectors (Donahue et al. (1998) *Nature Med.* 4:181-186; Shackleford et al. (1988) *Proc. Natl. Acad. Sci. USA* 85:9655-9659; U.S. Pat. Nos. 4,405,712, 4,650,764 and 5,252,479, and PCT Patent Publication Nos. WO 92/07573, WO 90/06997, WO 89/05345, WO 92/05266 and WO 92/14829; and lentivirus vectors (Kafri et al. (1997) *Nature Genetics* 17:314-317), as well as viruses that are replication-competent conditional to a cancer cell such as oncolytic herpes virus NV 1066 and vaccinia virus GLV-1h68, as described in U.S. Patent Application Pub. No. 2009/0311664. In particular, adenoviral vectors may be used, e.g. targeted viral vectors such as those described in U.S. Patent Application Pub. No. 2008/0213220. Accordingly, in some aspects, a viral vector comprises the nucleic acid construct wherein the viral vector is selected from the group consisting of adenoviral, lentiviral, retroviral, adeno-associated viral, and herpes simplex viral.

Exemplary non-viral vectors that may be employed include but are not limited to, for example: cosmids or plasmids; and, particularly for cloning large nucleic acid molecules, bacterial artificial chromosome vectors (BACs) and yeast artificial chromosome vectors (YACs); as well as liposomes (including targeted liposomes); cationic polymers; ligand-conjugated lipoplexes; polymer-DNA complexes; poly-L-lysine-molossin-DNA complexes; chitosan-DNA nanoparticles; polyethylenimine (PEI, e.g. branched PEI)-DNA complexes; various nanoparticles and/or nanoshells such as multifunctional nanoparticles, metallic nanoparticles or shells (e.g. positively, negatively or neutral charged gold particles, cadmium selenide, etc.); ultrasound-mediated microbubble delivery systems; various dendrimers (e.g. polyphenylene and poly(amidoamine)-based dendrimers; etc. In still further aspects, the non-viral vector is a nanoparticle is selected from the group consisting of: a liposome, an exosome, a nanodiamond, a polyphosphazene, a dendrimer, a polyplex, a lipoplex, a polymeric nanoconjugate, a high density lipoprotein (HDL), a fluorescent super paramagnetic iron oxide nanoparticle (FSPION), a gel (e.g., chitosan or gelatin), a block copolymer micelle, and an inversion emulsion. Exemplary polyplexes include, e.g., a polyethylenimine (PEI), a polypropylenimine (PPI), a poly-L-lysine (PLL), a Poly(amidoamine) (PAMAM), and a poly (2-dimethylaminoethyl methacrylate) (PDMAEMA). Exemplary lipoplexes include, e.g., 1,2-di-O-octadecenyl-3-trimethylammonium propane (DOTMA), 1,2-dioleoyl-3-trimethylammonium-propane (DOTAP), 1,2-dimyristyloxypropyl-3-dimethyl-hydroxyethyl ammonium bromide (DMRIE), 3β-[N—(N',N'-dimethylaminoethane)-carbamoyl]cholesterol hydrochloride (DC-Chol), Lipdi 67, dioctadecylaminoglycylcarboxyspermine (DOGS), and 2,3-dioleyloxy-N-[2(sperminecarboxamido)ethyl]-N,N-dimethyl-1-propanaminium trifluoroacetate (DOSPA).

Those of skill in the art will recognize that the choice of a particular vector will depend on its precise usage. Typically, one would not use a vector that integrates into the host cell genome due to the risk of insertional mutagenesis, and one should design vectors so as to avoid or minimize the occurrence of recombination within a vector's nucleic acid sequence or between vectors.

Accordingly, in some aspects, the nucleic acid construct is selected from the group consisting of adenoviral, lentiviral, retroviral, adeno-associated viral, and herpes simplex viral.

Host cells which contain the constructs and vectors of the presently disclosed subject matter are also encompassed, e.g. in vitro cells such as cultured cells, or bacterial or insect cells which are used to store, generate or manipulate the vectors, and the like. Accordingly, in yet another aspect, cells, particularly cancer cells, comprising the tripartite nucleic acid construct are also provided. The constructs and vectors may be produced using recombinant technology or by synthetic means.

The constructs of the presently disclosed subject matter include at least one transcribable element (e.g. a gene composed of sequences of nucleic acids) that is operably connected or linked to a promoter that specifically or selectively drives transcription within cancer cells.

As used herein, the term "operably linked" means that a nucleic acid sequence or protein is placed into a functional relationship with another nucleic acid sequence or protein. For example, a promoter sequence is operably linked to a coding sequence if the promoter promotes transcription of the coding sequence. As a further example, a repressor protein and a nucleic acid sequence are operably linked if the repressor protein binds to the nucleic acid sequence. Additionally, a protein may be operably linked to a first and a second nucleic acid sequence if the protein binds to the first nucleic acid sequence and so influences transcription of the second, separate nucleic acid sequence. Generally, "operably linked" means that DNA sequences being linked are contiguous, although they need not be, and that a gene and a regulatory sequence or sequences (e.g., a promoter) are connected in such a way as to permit gene expression when the appropriate molecules (e.g., transcriptional activator proteins~transcription factors~or proteins which include transcriptional activator domains) are bound to the regulatory sequence or sequences.

Expression of the transcribable element may be inducible or constitutive. Suitable cancer selective/specific promoters (and or promoter/enhancer sequences) that may be used include but are not limited to: PEG-Prom, astrocyte elevated gene 1 (AEG-1) promoter, survivin-Prom, human telomerase reverse transcriptase (hTERT)-Prom, hypoxia-inducible promoter (HIF-1-alpha), DNA damage inducible promoters (e.g. GADD promoters), metastasis-associated promoters (metalloproteinase, collagenase, etc.), ceruloplasmin promoter (Lee et al. (2004) *Cancer Res.* 64:1788), mucin-1 promoters such as DF3/MUC1 (see U.S. Pat. No. 7,247,297), HexII promoter as described in U.S. Patent App. Pub. No. 2001/00111128; prostate-specific antigen enhancer/promoter (Rodriguez et al. (1997) *Cancer Res.* 57:2559-2563); α-fetoprotein gene promoter (Hallenbeck et al. (1999) *Hum. Gene Ther.* 10:1721-1733); the surfactant protein B gene promoter (Doronin et al. (2001) *J. Virol.* 75: 3314-3324); MUC1 promoter (Kurihara et al. (2000) *J. Clin. Investig.* 106: 763-771); H19 promoter (U.S. Pat. No. 8,034, 914); promoters described in U.S. Pat. Nos. 7,816,131, 6,897,024, 7,321,030, 7,364,727; as well as derivative forms thereof.

Any promoter that is specific for driving gene expression only in cancer cells, or that is selective for driving gene expression in cancer cells, or at least in cells of a particular type of cancer (so as to treat and image e.g. prostate, colon, breast, etc. primary and metastatic cancer) may be used in the practice of the invention. By "specific for driving gene expression in cancer cells" is meant that the promoter, when operably linked to a gene, functions to promote transcription of the gene only when located within a cancerous, malignant cell, but not when located within normal, non-cancerous cells. By "selective for driving gene expression in cancer cells" is meant that the promoter, when operably linked to a gene, functions to promote transcription of the gene to a greater degree when located within a cancer cell, than when located within non-cancerous cells. For example, the promoter drives gene expression of the gene at least about 2-fold, or about 3-, 4-, 5-, 6-, 7-, 8-, 9-, or 10-fold, or even about 20-, 30-, 40-, 50-, 60-, 70-, 80-, 90- or 100-fold or more (e.g. 500- or 1000-fold) when located within a cancerous cell than when located within a non-cancerous cell, when measured using standard gene expression measuring techniques that are known to those of skill in the art.

In one embodiment, the promoter is the PEG-Prom promoter or a functional derivative thereof. This promoter is described in detail, for example, in U.S. Pat. No. 6,737,523, the complete contents of which are herein incorporated by reference. Nucleotide sequences which display homology to the PEG-Prom promoter are also encompassed for use, e.g. those which are at least about 50, 60, 70, 75, 80, 85, 90, 95, 96, 97, 98, or 99% homologous, as determined by standard nucleotide sequence comparison programs which are known in the art.

In another aspect, the third promoter is a constitutive promoter, particularly wherein the third promoter is cytomegalovirus (CMV). In a further aspect, the third promoter is a cancer-selective promoter. In a still further aspect, the therapeutic agent is selected from the group consisting of an anti-cancer agent, an apoptosis inducing agent, a tumor suppressor agent, an immune system enhancing agent, and an immunomodulatory agent, particularly wherein the therapeutic agent is an immunomodulatory cytokine, and more particularly wherein the immunomodulatory cytokine is mda-7/IL-24 or a truncated variant thereof such as M4.

In some embodiments, the presently disclosed subject matter provides nucleic acid constructs for use in imaging cancer cells and tumors. The constructs include at least one transcribable element that is either directly detectable using imaging technology, or which functions with one or more additional molecules in a manner that creates a signal that is detectable using imaging technology. The transcribable element is operably linked to a cancer selective/specific promoter as described above, and is generally referred to as a "reporter" molecule. Reporter molecules can cause production of a detectable signal in any of several ways: they may encode a protein or polypeptide that has the property of being detectable in its own right; they may encode a protein or polypeptide that interacts with a second substance and causes the second substance to be detectable; they may encode a protein or polypeptide that sequesters a detectable substance, thereby increasing its local concentration sufficiently to render the surrounding environment (e.g. a cancer cell) detectable. If the gene product of the reporter gene interacts with another substance to generate a detectable signal, the other substance is referred to herein as a "complement" of the reporter molecule.

Examples of reporter proteins or polypeptides that are detectable in their own right (directly detectable) include those which exhibit a detectable property when exposed to, for example, a particular wavelength or range of wavelengths of energy. Examples of this category of detectable proteins include but are not limited to: green fluorescent protein (GFP) and variants thereof, including mutants such as blue, cyan, and yellow fluorescent proteins; proteins which are engineered to emit in the near-infrared regions of the spectrum; proteins which are engineered to emit in the short-, mid-, long-, and far-infrared regions of the spectrum; etc. Those of skill in the art will recognize that such detectable proteins may or may not be suitable for use in humans, depending on the toxicity or immunogenicity of the reagents involved. However, this embodiment has applications in, for example, laboratory or research endeavors involving animals, cell culture, tissue culture, various ex vivo procedures, etc.

Another class of reporter proteins includes those which function with a complement molecule. In this embodiment, a construct comprising a gene encoding a reporter molecule is administered systemically to a subject in need of imaging, and a molecule that is a complement of the reporter is also administered systemically to the subject, before, after or together with the construct. If administered prior to or after administration of the construct, administration of the two may be timed so that the diffusion of each entity into cells, including the targeted cancer cells, occurs in a manner that results in sufficient concentrations of each within cancer cells to produce a detectable signal, e.g. typically within about 1 hour or less. If the two are administered "together", then separate compositions may be administered at the same or nearly the same time (e.g. within about 30, 20, 15, 10, or 5 minutes or less), or a single composition comprising both the construct and the complement may be administered. In any case, no interaction between the reporter and the complement can occur outside of cancer cells, because the reporter is not produced and hence does not exist in any other location, since its transcription is controlled by a cancer specific/selective promoter.

One example of this embodiment is the oxidative enzyme luciferase and various modified forms thereof, the complement of which is luciferin. Briefly, catalysis of the oxidation of its complement, luciferin, by luciferase produces readily detectable amounts of light. Those of skill in the art will recognize that this system is not generally used in humans due to the need to administer the complement, luciferin to the subject. However, this embodiment is appropriate for use in animals, and in research endeavors involving cell culture, tissue culture, and various ex vivo procedures.

Another exemplary protein of this type is thymidine kinase (TK), e.g. TK from herpes simplex virus 1 (HSV 1), or from other sources. TK is a phosphotransferase enzyme (a kinase) that catalyzes the addition of a phosphate group from ATP to thymidine, thereby activating the thymidine for incorporation into nucleic acids, e.g. DNA. Various analogs of thymidine are also accepted as substrates by TK, and radiolabeled forms of thymidine or thymidine analogs may be used as the complement molecule to reporter protein TK. Without being bound by theory, it is believed that once phosphorylated by TK, the radiolabeled nucleotides are retained intracellularly because of the negatively charged phosphate group; or, alternatively, they may be incorporated into e.g. DNA in the cancer cell, and thus accumulate within the cancer cell. Either way, they provide a signal that is readily detectable and distinguishable from background radioactivity. Also, the substrate that is bound to TK at the time of imaging provides additional signal in the cancer cell. In fact, mutant TKs with very low Kms for substrates may augment this effect by capturing the substrate. The radioactivity emitted by the nucleotides is detectable using a variety of techniques, as described herein. This aspect of the use of TK harnesses the labeling potential of this enzyme; the toxic capabilities of TK are described below.

Various TK enzymes or modified or mutant forms thereof may be used in the practice of the invention, including but not limited to: HSV1-TK, HSV1-sr39TK, mutants with increased or decreased affinities for various substrates, temperature sensitive TK mutants, codon-optimized TK, the mutants described in U.S. Pat. No. 6,451,571 and U.S. Patent App. Pub. No. 2011/0136221, both of which are herein incorporated by reference; as well as various suitable human TKs and mutant human TKs. Detectable TK substrates that may be used include but are not limited to: thymidine analogs such as: "fialuridine" i.e. [1-(2-deoxy-2-fluoro-1-D-arabinofuranosyl)-5-iodouracil], also known as "FIAU" and various forms thereof, e.g. 2'-fluoro-2'-deoxy-β-D-5-[$^{125}$I]iodouracil-arabinofuranoside ([$^{125}$I] FIAU), [$^{124}$I]FIAU; thymidine analogs containing o-carboranylalkyl groups at the 3-position, as described by Al Mahoud et al. (2004) *Cancer Res.* 64:6280), which may have a dual function in that they mediate cytotoxicity as well, as described below; hydroxymethyl]butyl)guanine (HBG) derivatives such as 9-(4-$^{18}$F-fluoro-3-[hydroxymethyl]butyl)guanine ($^{18}$F-FHBG); 2'-deoxy-2'-[$^{18}$F]-fluoro-1-beta-D-arabinofuranosyl-5-iodouracil($^{18}$F-FEAU), 2'-deoxy-2'-[$^{18}$F]-fluoro-5-methyl-β-L-arabinofuranosyluracil ($^{18}$F-FMAU),1-(2'-deoxy-2'-fluoro-beta-D-arabinofuranosyl)-5-[$^{18}$F]iodouracil($^{18}$F-FIAU), 2'-deoxy-2'-[$^{18}$F]-fluoro-1-beta-D-arabinofuranosyl-5-iodouracil ($^{18}$F-FIAC, see, for example, Chan et al. (2011) *Nuclear Medicine and Biology* 38:987-995; Cai et al. (2011) *Nuclear Medicine and Biology* 38:659-666); and various alkylated pyrimidine derivatives such as a C-6 alkylated pyrimidine derivative.

Other exemplary reporter molecules may retain or cause retention of a detectably labeled complement by any of a variety of mechanisms. For example, the reporter molecule may bind to the complement very strongly (e.g. irreversibly) and thus increase the local concentration of the complement within cancer cells; or the reporter molecule may modify the complement in a manner that makes egress of the complement from the cell difficult, or at least slow enough to result in a net delectable accumulation of complement within the cell; or the reporter may render the complement suitable for participation in one or more reactions which "trap" or secure the complement, or a modified form thereof that still includes the detectable label, within the cell, as is the case with the TK example presented above. One example of such a system would be an enzyme-substrate complex, in which the reporter is usually the enzyme and the complement is usually the substrate, although this need not always be the case: the reporter may encode a polypeptide or peptide that is a substrate for an enzyme that functions as the "complement". In some embodiments, the substrate is labeled with a detectable label (e.g. a radio-, fluorescent-, phosphorescent-, colorimetric-, light emitting-, or other label) and accumulates within cancer cells due to, for example, an irreversible binding reaction with the enzyme (i.e. it is a suicide substrate), or because it is released from the enzyme at a rate that is slow enough to result in a detectable accumulation within cancer cells, or the reaction with the enzyme causes a change in the properties of the substrate so that it cannot readily leave the cell, or leaves the cell very slowly (e.g. due to an increase in size, or a change in charge, hydrophobicity or hydrophilicity, etc.); or because, as a result of interaction or association with the enzyme, the substrate is modified and then engages in subsequent reactions which cause it (together with its detectable tag or label) to be retained in the cells.

Other proteins that may function as reporter molecules in the practice of the invention are transporter molecules which are located on the cell surface or which are transmembrane proteins, e.g. ion pumps which transport various ions across cell membranes and into cells. An exemplary ion pump is the sodium-iodide symporter (NIS) also known as solute carrier family 5, member 5 (SLC5A5). In nature, this ion pump actively transports iodide (I$^-$) across e.g. the basolateral membrane into thyroid epithelial cells. Recombinant forms of the transporter encoded by sequences of the constructs described herein may be selectively transcribed in cancer cells, and transport radiolabeled iodine into the cancer cells. Other examples of this family of transporters that may be used in the practice of the invention include but are not limited to norepinephrine transporter (NET); dopamine receptor; various estrogen receptor systems), ephrin proteins such as membrane-anchored ephrin-A (EFNA) and the transmembrane protein ephrin-B (EFNB); epidermal growth factor receptors (EGFRs); insulin-like growth factor receptors (e.g. IGF-1, IGF-2), etc.); and transforming growth factor (TGF) receptors such as TGFα. In these cases, the protein or a functional modified form thereof is expressed by the vector of the invention and the ligand molecule is administered to the patient. Usually, the ligand is labeled with a detectable label as described herein, or becomes detectable upon association or interaction with the transporter. In some embodiments, detection may require the association of a third entity with the ligand, e.g. a metal ion. The ligand may also be a protein, polypeptide or peptide.

In addition, antibodies may be utilized in the practice of the invention. For example, the vectors of the invention may be designed to express proteins, polypeptides, or peptides which are antigens or which comprise antigenic epitopes for which specific antibodies have been or can be produced. Exemplary antigens include but are not limited to tumor specific proteins that have an abnormal structure due to mutation (protooncogenes, tumor suppressors, the abnormal products of ras and p53 genes, etc.); various tumor-associated antigens such as proteins that are normally produced in very low quantities but whose production is dramatically increased in tumor cells (e.g. the enzyme tyrosinase, which is elevated in melanoma cells); various oncofetal antigens (e.g. alphafetoprotein (AFP) and carcinoembryonic antigen (CEA); abnormal proteins produced by cells infected with oncoviruses, e.g. EBV and HPV; and various cell surface glycolipids and glycoproteins which have abnormal structures in tumor cells. The antibodies, which may be monoclonal or polyclonal, are labeled with a detectable label and are administered to the patient after or together with the vector. The antibodies encounter and react with the expressed antigens or epitopes, which are produced only (or at least predominantly) in cancer cells, thereby labeling the cancer cells. Conversely, the antibody may be produced by the vector of the invention, and a labeled antigen may be administered to the patient. In this embodiment, an antibody or a fragment thereof, e.g. a Fab (fragment, antigen binding) segment, or others that are known to those of skill in the art, are employed. In this embodiment, the antigen or a substance containing antigens or epitopes for which the antibody is specific is labeled and administered to the subject being imaged.

Other examples of such systems include various ligand binding systems such as reporter proteins/polypeptides that bind ligands which can be imaged, examples of which include but are not limited to: proteins (e.g. metalloenzymes) that bind or chelate metals with a detectable signal; and ferritin-based iron storage proteins. Such systems of reporter and complement may be used in the practice of the presently disclosed subject matter, provided that the reporter or the complement can be transcribed under control of a cancer promoter, and that the other binding partner is detectable or can be detectably labeled, is administrable to a subject, and is capable of diffusion into cancer cells. Those of skill in the art will recognize that some such systems are suitable for use e.g. in human subjects, while other are not due to, for example, toxicity. However, systems in the latter category may be well-suited for use in laboratory settings.

In yet other embodiments, the cancer-specific or cancer-selective promoters in the vectors of the invention drive expression of a secreted protein that is not normally found in the circulation. In this embodiment, the presence of the protein may be detected by standard (even commercially available) methods with high sensitivity in serum or urine. In other words, the cancer cells that are detected are detected in a body fluid.

In yet other embodiments, the cancer-specific or cancer-selective promoters in the vectors of the invention drive transcription of a protein or antigen to be expressed on the cell surface, which can then be tagged with a suitable detectable antibody or other affinity reagent. Candidate proteins for secretion and cell surface expression include but are not limited to: β-subunit of human chorionic gonadotropin (β hCG); human α-fetoprotein (AFP); and streptavidin (SA).

β hCG is expressed in pregnant women and promotes the maintenance of the corpus luteum during the beginning of pregnancy. The level of β hCG in non-pregnant normal women and men is 0-5 mIU/mL. hCG is secreted into the serum and urine and β hCG has been used for pregnancy test since the α-subunit of hCG is shared with other hormones. Urine β hCG can be easily detected by a chromatographic immunoassay (i.e. pregnancy test strip, detection threshold is 20-100 mIU/mL) at home-physician's office- and laboratory-based settings. The serum level can be measured by chemiluminescent or fluorescent immunoassays using 2-4 mL of venous blood for more quantitative detection. β hCG has been shown to secreted into the media when it was expressed in monkey cells. Human AFP is an oncofetal antigen that is expressed only during fetal development and in adults with certain types of cancers. AFP in adults can be found in hepatocellular carcinoma, testicular tumors and metastatic liver cancer. AFP can be detected in serum, plasma, or whole blood by chromatographic immunoassay and by enzyme immunoassay for the quantitative measurement.

Strepavadin (SA) can also be used as a cell surface target in the practice of the invention. The unusually high affinity of SA with biotin provides very efficient and powerful target for imaging and therapy. To bring SA to the plasma membrane of the cancer cells, SA can be fused to glycosylphosphatidylinositol (GPI)-anchored signal of human CD14. GPI-anchoring of SA will be suitable for therapeutic applications since GPI-anchor proteins can be endocytosed to the recycling endosomes. Once expressed on the cell surface, SA can then be bound by avidin conjugates that contain a toxic or radiotoxic warhead. Toxic proteins and venoms such as ricin, abrin, *Pseudomonas* exotoxin (PE, such as PE37, PE38, and PE40), diphtheria toxin (DT), saporin, restrictocin, cholera toxin, gelonin, *Shigella* toxin, and pokeweed antiviral protein, *Bordetella pertussis* adenylate cyclase toxin, or modified toxins thereof, or other toxic agents that directly or indirectly inhibit cell growth or kill cells may be linked to avidin; as could toxic low molecular weight species, such as doxorubicin or taxol or radionuclides such as $^{125}$I, $^{131}$I, $^{111}$In, $^{177}$Lu, $^{211}$At, $^{225}$Ac, $^{213}$Bi and $^{90}$Y; antiangiogenic agents such as thalidomide, angiostatin, anti-sense molecules, COX-2 inhibitors, integrin antagonists, endostatin, thrombospondin-1, and interferon alpha, vitaxin, celecoxib, rofecoxib; as well as chemotherapeutic agents such as: pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as *vinca* alkaloids (vinblastine, vincristine, and vinorelbine), microtubule disruptors such as taxane (paclitaxel, docetaxel), vincristin, vinblastin, nocodazole, epothilones and navelbine, epipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers; caspase activators; and chromatin disruptors, especially those which can be conjugated to nanoparticles.

The detectable components of the system (usually a complement or substrate) used in the imaging embodiment of the invention may be labeled with any of a variety of detectable labels, examples of which are described above. In addition, especially useful detectable labels are those which are highly sensitive and can be detected non-invasively, such as the isotopes $^{124}$I, $^{123}$I, $^{99}$mTc, $^{18}$F, $^{86}$Y, $^{11}$C, $^{125}$I, $^{64}$Cu, $^{67}$Ga, $^{68}$Ga, $^{201}$Tl, $^{76}$Br, $^{75}$Br, $^{111}$In, $^{82}$Rb, $^{13}$N and others.

Those of skill in the art will recognize that many different detection techniques exist which may be employed in the practice of the present invention, and that the selection of one particular technique over another generally depends on the type of signal that is produced and also the medium in which the signal is being detected, e.g. in the human body, in a laboratory animal, in cells or tissue culture, ex vivo, etc. For example, bioluminescence imaging (BLI); fluorescence imaging; magnetic resonance imaging [MRI, e.g. using lysine rich protein (LRp) as described by Gilad et al. (2007) *Nature Biotechnology* 25:2; or creatine kinase, tyrosinase, β-galactosidase, iron-based reporter genes such as transferring, ferritin, and MagA; low-density lipoprotein receptor-related protein (LRP; polypeptides such as poly-L-lysine, poly-L-arginine and poly-L-threonine; and others as described, e.g. by Gilad et al. (2008) *J. Nucl. Med.* 49(12): 1905-1908); computed tomography (CT); positron emission tomography (PET); single-photon emission computed tomography (SPECT); boron neutron capture; for metals: synchrotron X-ray fluorescence (SXRF) microscopy, secondary ion mass spectrometry (SIMS), and laser ablation inductively coupled plasma mass spectrometry (LA-ICP-MS) for imaging metals; photothermal imaging (using for example, magneto-plasmonic nanoparticles, etc.

One of skill in the art will understand that variants of any of the polynucleotides or polypeptides described herein may also be used within the compositions and methods of the presently disclosed subject matter. Variants of polynucleotides or polypeptides, as the term is used herein, are polynucleotides or polypeptides that differ from a reference polynucleotide or polypeptide. For example, a variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical. A fragment or truncation refers to a sequence of reduced length relative to the reference sequence and comprising, over the common portion, a sequence identical to the reference sequence.

II. Diagnostic and Therapeutic Methods

In another aspect of the presently disclosed subject matter, a method of imaging and treating cancerous cells in a subject is provided, comprising the steps of: a) administering to the subject a tripartite nucleic acid construct comprising a first promoter operably linked to at least one gene required for viral replication, a second promoter operably linked to a gene encoding an imaging agent, and a third promoter operably linked to a gene encoding a therapeutic agent, wherein the first promoter and the second promoter are each cancer-selective; and b) imaging cancerous cells in the subject by detecting a detectable signal from the imaging agent, wherein the gene encoding the therapeutic agent is expressed in the cancerous cells.

Targeted cancer therapy may be carried out by administering the constructs as described herein to a subject in need thereof. In this embodiment, a gene encoding a therapeutic molecule, e.g. a protein or polypeptide, which is deleterious to cancer cells is operably linked to a cancer-specific promoter as described herein in a "therapeutic construct" or "therapeutic vector". The therapeutic protein may kill cancer cells (e.g. by initiating or causing apoptosis), or may slow their rate of growth (e.g. may slow their rate of proliferation), or may arrest their growth and development or otherwise damage the cancer cells in some manner, or may even render the cancer cells more sensitive to other anti-cancer agents.

Genes encoding therapeutic molecules that may be employed in the present invention include but are not limited to suicide genes, including genes encoding various enzymes; oncogenes; tumor suppressor genes; toxins; cytokines; oncostatins; TRAIL, and the like. Exemplary enzymes include, for example, thymidine kinase (TK) and various derivatives thereof; TNF-related apoptosis-inducing ligand (TRAIL), xanthine-guanine phosphoribosyltransferase (GPT); cytosine deaminase (CD); hypoxanthine phosphoribosyl transferase (HPRT); and the like. Exemplary tumor suppressor genes include neu, EGF, ras (including H, K, and N ras), p53, Retinoblastoma tumor suppressor gene (Rb), Wilm's Tumor Gene Product, Phosphotyrosine Phosphatase (PTPase), AdE1A and nm23 Suitable toxins include *Pseudomonas* exotoxin A and S; diphtheria toxin (DT); *E. coli* LT toxins, Shiga toxin, Shiga-like toxins (SLT-1, -2), ricin, abrin, supporin, gelonin, and the like. Suitable cytokines include interferons and interleukins such as interleukin 1 (IL-1), IL-2, IL-3, IL-4, IL-5, IL-6, IL-7, IL-8, IL-9, IL-10, IL-11, IL-12, IL-13, IL-14, IL-15, LL-18, β-interferon, α-interferon, γ-interferon, angiostatin, thrombospondin, endostatin, GM-CSF, G-CSF, M-CSF, METH 1, METH 2, tumor necrosis factor, TGFβ, LT and combinations thereof. Other anti-tumor agents include: GM-CSF interleukins, tumor necrosis factor (TNF); interferon-beta and virus-induced human Mx proteins; TNF alpha and TNF beta; human melanoma differentiation-associated gene-7 (mda-7), also known as interleukin-24 (IL-24), various truncated versions of mda-7/IL-24 such as M4; siRNAs and shRNAs targeting important growth regulating or oncogenes which are required by or overexpressed in cancer cells; antibodies such as antibodies that are specific or selective for attacking cancer cells; and the like.

In some embodiments, the invention provides cancer treatment protocols in which imaging of cancer cells and tumors is combined with treating the disease, i.e. with killing, destroying, slowing the growth of, attenuating the ability to divide (reproduce), or otherwise damaging the cancer cells. These protocols may be referred to herein as "theranostics" or "combined therapies" or "combination protocols", or by similar terms and phrases.

In some embodiments, the combined therapy involves administering to a cancer patient a gene construct (e.g. a plasmid) that comprises, in a single construct, both a reporter gene (for imaging) and at least one therapeutic gene of interest (for treating the disease). In this embodiment, expression of either the reporter gene or the therapeutic gene, or preferably both is mediated by a cancer cell specific or selective promoter as described herein. Preferably, two different promoters are used in this embodiment in order to prevent or lessen the chance of crossover and recombination within the construct. Alternatively, tandem translation mechanisms may be employed, for example, the insertion of one or more internal ribosomal entry site (IRES) into the construct, which permits translation of multiple mRNA transcripts from a single mRNA. In this manner, both a reporter protein/polypeptide and a protein/polypeptide that is lethal or toxic to cancer cells are selectively or specifically produced within the targeted cancer cells.

Alternatively, the polypeptides encoded by the constructs of the invention (e.g. vectors) may be genetically engineered to contain a contiguous sequence comprising two or more polypeptides of interest (e.g. a reporter and a toxic agent) with an intervening sequence that is cleavable within the cancer cell, e.g. a sequence that is enzymatically cleaved by intracellular proteases, or even that is susceptible to non-enzymatic hydrolytic cleavage mechanisms. In this case, cleavage of the intervening sequence results in production of functional polypeptides, i.e. polypeptides which are able to carry out their intended function, e.g. they are at least 50, 60, 70, 80, 90, or 100% (or possible more) as active as the protein sequences on which they are modeled or from which they are derived (e.g. a sequence that occurs in nature), when measured using standard techniques that are known to those of skill in the art.

In other embodiments of combined imaging and therapy, two different vectors may be administered, one of which is an "imaging vector or construct" as described herein, and the other of which is a "therapeutic vector or construct" as described herein.

In other embodiments of combined imaging and therapy, the genes of interest are encoded in the genome of a viral vector that is capable of transcription and/or translation of multiple mRNAs and/or the polypeptides or proteins they encode, by virtue of the properties inherent in the virus. In this embodiment, such viral vectors are genetically engineered to contain and express genes of interest (e.g. a gene required for viral replication, a reporter gene, and a therapeutic gene) under the principle control of one or more cancer specific promoters.

The presently disclosed subject matter provides compositions that comprise one or more vectors or constructs as described herein and a pharmacologically suitable carrier. The compositions are typically for systemic administration. The preparation of such compositions is known to those of skill in the art. Typically, such compositions are prepared either as liquid solutions or suspensions, or as solid forms suitable for solution in, or suspension in, liquids prior to administration. The preparation may also be emulsified. The active ingredients may be mixed with excipients, which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any of one or more ingredients known in the art to provide the composition in a form suitable for administration. The final amount of vector in the formulations may vary. However, in general, the amount in the formulations will be from about 1-99%.

The vector compositions (or preparations) of the present invention are typically administered systemically, although this need not always be the case, as localized administration (e.g. intratumoral, or into an external orifice such as the vagina, the nasopharygeal region, the mouth; or into an internal cavity such as the thoracic cavity, the cranial cavity, the abdominal cavity, the spinal cavity, etc.) is also included. For systemic distribution of the vector, the preferred routes of administration include but are not limited to: intravenous, by injection, transdermal, via inhalation or intranasally, or via injection or intravenous administration of a cationic polymer-based vehicle (e.g. vivo-jetPEI®). Liposomal delivery, which when combined with targeting moieties will permit enhanced delivery.

The ultrasound-targeted microbubble-destruction technique (UTMD) may also be used to deliver imaging and theranostic agents (Dash et al. (2011) *Proc. Natl. Acad. Sci. USA.* 108(21):8785-90); hydroxyapatite-chitosan nanocomposites (Venkatesan et al. *Biomaterials.* 2011 May; 32(15): 3794-806); and others (Dash et al. (2011) *Discov. Med.* 11(56):46-56); and the like. Any method that is known to those of skill in the art, and which is commensurate with the type of construct that is employed, may be utilized. In addition, the compositions may be administered in conjunction with other treatment modalities known in the art, such as various chemotherapeutic agents such a Pt drugs, substances that boost the immune system, antibiotic agents, and the like; or with other detections and imaging methods (e.g. to confirm or provide improved or more detailed imaging, e.g. in conjunction with mammograms, X-rays, Pap smears, prostate specific antigen (PSA) tests, and the like.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Those of skill in the art will recognize that the amount of a construct or vector that is administered will vary from subject to subject, and possibly from administration to administration for the same subject, depending on a variety of factors, including but not limited to: weight, age, gender, overall state of health, the particular disease being treated, and other factors, and the amount and frequency of administration is best established by a health care professional such as a physician. Typically, optimal or effective tumor-inhibiting or tumor-killing amounts are established e.g. during animal trials and during standard clinical trials. Those of skill in the art are familiar with conversion of doses e.g. from a mouse to a human, which is generally done through body surface area, as described by Freireich et al. (1966) *Cancer Chemother Rep.* 50(4):219-244).

In general, for treatment methods, the amount of a vector such as a plasmid will be in the range of from about 0.01 to about 5 mg/kg or from about 0.05 to about 1 mg/kg (e.g. about 0.1 mg/kg), and from about $10^5$ to about $10^{20}$ infectious units (Ws), or from about $10^8$ to about $10^{13}$ IUs for a viral-based vector. In general, for imaging methods, the amount of a vector will be in the range of from about 0.01 to about 5 mg/kg or from about 0.05 to about 1 mg/kg (e.g. about 0.1 mg/kg) of e.g. a plasmid, and from about $10^5$ to about $10^{20}$ infectious units (IUs), or from about $10^8$ to about $10^{13}$ IUs for a viral-based vector. For combined imaging and therapy, the amounts of a vector will be in the ranges described above. Those of skill in the art are familiar with calculating or determining the level of an imaging signal that is required for adequate detection. For example, for radio-pharmaceuticals such as [$^{124}$I]FIAU, an injection on the order or from about 1 mCi to about 10 mCi, and usually about 5 mCi, (i.e. about 1 mg of material) is generally sufficient.

Further, one type of vector or more than one type of vector may be administered in a single administration, e.g. a therapy vector plus an imaging vector, or two (or more) different therapy vectors (e.g. each of which have differing modes of action so as to optimize or improve treatment outcomes), or two or more different imaging vectors, etc.

Cancer treatment may require repeated administrations of the compositions. For example, administration may be daily or every few days, (e.g. every 2, 3, 4, 5, or 6 days), or weekly, bi-weekly, or every 3-4 weeks, or monthly, or any combination of these, or alternating patterns of these. For example, a "round" of treatment (e.g. administration one a week for a month) may be followed by a period of no administration for a month, and then followed by a second round of weekly administration for a month, and so on, for any suitable time periods, as required to optimally treat the subject.

Imaging methods also may be carried out on a regular basis, especially when a subject is known or suspected to be at risk for developing cancer, due to e.g., the presence of a particular genetic mutation, family history, exposure to carcinogens, previous history of cancer, advanced age, and the like. For example, annual, semi-annual, or bi-annual, or other periodic monitoring may be considered prudent for such individuals. Alternatively, individuals with no risk factors may simply wish to be monitored as part of routine health care, in order to rule out the disease.

The subjects or patients to whom the compositions of the invention are administered are typically mammals, frequently humans, but this need not always be the case. Veterinary applications are also contemplated. Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like).

The constructs and methods of the invention are not specific for any one type of cancer. By "cancer" is meant malignant neoplasms in which cells divide and grow uncontrollably, forming malignant tumors, and invade nearby parts of the body. Cancer may also spread or metastasize to more distant parts of the body through the lymphatic system or bloodstream. The constructs and methods of the invention may be employed to image, diagnose, treat, monitor, etc. any type of cancer, tumor, neoplastic or tumor cells including but not limited to: osteosarcoma, ovarian carcinoma, breast carcinoma, melanoma, hepatocarcinoma, lung cancer, brain cancer, colorectal cancer, hematopoietic cell, prostate cancer, cervical carcinoma, retinoblastoma, esophageal carcinoma, bladder cancer, neuroblastoma, renal cancer, gastric cancer, pancreatic cancer, and the like.

In addition, the presently disclosed subject matter may also be applied to imaging and therapy of benign tumors, which are generally recognized as not invading nearby tissue or metastasizing, for example, moles, uterine fibroids, and the like.

III. Ultrasound Targeted Microbubble Population Compositions and Methods

In another aspect of the presently disclosed subject matter, a composition comprising an ultrasound targeted microbubble population is provided, wherein the microbubble population stably binds a tripartite nucleic acid construct, and wherein the tripartite nucleic acid construct comprises a first promoter operably linked to at least one gene required for viral replication, a second promoter operably linked to a gene encoding an imaging agent, and a third promoter operably linked to a gene encoding a therapeutic agent, wherein the first promoter and the second promoter are each cancer-selective.

In a further aspect, a method for delivering a tripartite nucleic acid construct to cancerous cells in a subject is provided, comprising the steps of: a) providing an ultrasound targeted microbubble population stably binding the tripartite nucleic acid construct; b) providing an ultrasound device capable of directing the microbubble population to the cancer cells; c) directing the microbubble population to the cancer cells with the ultrasound device; and d) bursting the microbubble population under conditions such that the tripartite nucleic acid construct is delivered to the cancer cells; wherein the tripartite nucleic acid construct comprises a first promoter operably linked to at least one gene required for viral replication, a second promoter operably linked to a gene encoding an imaging agent, and a third promoter operably linked to a gene encoding a therapeutic agent, wherein the first promoter and the second promoter are each cancer-selective.

As used herein, the term "microbubble" refers to any spherical arrangement of lipids creating an outer shell and an inner void space. The lipid layer may be modified to bind molecules in a stable manner.

The use of microbubbles as gene vectors utilizes destruction of DNA-loaded microbubbles by a focused ultrasound beam during their microvascular transit through the target area, resulting in localized transduction upon disruption of the microbubble shell, while sparing non-targeted areas (see U.S. Patent App. Pub. No. 2013204166). Ultrasound/Microbubble Targeted Delivery (UMTD) has been used to deliver genes to cells in vitro, and more recently, has been employed to deliver genes in vivo to treat diabetes and cardiovascular disease in experimental animal models (Chen et al. (2007) *Gene Ther.* 14:1102-1110; Fujii et al. (2009) *J. Am. Coll. Cardiol. Cardiovasc. Imaging* 2:869-879).

In some embodiments, the microbubbles are gene or molecular therapy vectors. The use of microbubbles as gene vectors has advantages over viral systems. During UMTD, intravenously injected microbubbles can be destroyed as they transit through the microcirculation of the target site where the ultrasound beam is directed, functionally achieving selective payload delivery without the need for invasive approaches such as direct intratumor injection. The lipid microbubbles we used for UMTD have no viral proteins, and can theoretically be administered repetitively. Additionally, because the microbubbles are ultrasound contrast agents, it is possible to simultaneously image microbubble transit through the tumor, thereby enabling more precise real time guidance of plasmid delivery.

As used herein, the "bursting threshold" refers to any acoustic frequency that results in the lipid shell breakdown of a microbubble population, thereby releasing the stably bound nucleic acids. Such acoustic frequencies are usually generated by an ultrasound device operating at a frequency ranging between approximately 0.25-5 MHz, preferably between approximately 0.5-2.5 MHz, but more preferably between approximately 0.75-2.0 mHz, and most preferably between 1.0-1.5 MHz. For example, a bursting threshold of UMTD microbubbles may be approximately between 1.3-1.4 MHz.

IV. General Definitions

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Construction of a Tripartite Therasnostic Virus: Ad5.PEG-E1A-CCN1-Luc2-CMV-mda-7 (TCTV-Luc7)

A conditionally-replicative adenovirus vector containing the E1A/B (E1A/E1B) region under the control of a PEG promoter and two expression cassettes in the E3 region (CCN1-Luc2 and CMV-mda-7) were constructed using the AdenoQuick1.0 system (FIG. 1).

The shuttle plasmid for inserting the PEG promoter upstream of the E1A/B coding sequences (pPEG-pE1.2) was constructed by Dr. Sarkar and has already been used successfully to construct other vectors. The shuttle plasmid for inserting the CCN1 promoter driven luciferase and CMV promoter driven mda-7/IL-24 were generated as follows:

Generating pCCNJ-luciferase-SV40 pA-pE3.1: pCCNJ was PCR amplified using primers, sense: 5'-AAGGAAAAAAGCGGCCG CAAAACAAACAAG-TACAACATAC-3' (SEQ ID NO:1) and antisense: 5'-GTA-CACGCGTCGAC GGCGCCCCGGAGCCCGCCTTT-3 (SEQ ID NO:2); Luciferase was amplified from pGL4.14 (Promega) using primers, sense: 5'-GTACACGCGTC-GACGCCGCCATGGAA GATGCCAAAAACA-3' (SEQ ID NO:3) and antisense: 5' ATCGCGGATCCTTACACG-GCGATCTTGCCG-3' (SEQ ID NO:4); and SV40 poly A was PCR amplified using primers, sense: 5'-ATCGCG-GATCCGAG ATTTCGATTCCACCG-3' (SEQ ID NO:5) and antisense: 5'-GGACTAGTCAGGCTTTACACTT-TATGC-3' (SEQ ID NO:6). The E3 region specific shuttle vector pE3.1 and the SV40 polyA PCR product were digested using BamHI and SpeI and ligated. The shuttle vector containing the poly A tail was next digested with NotI and BamHI, the pCCNJ PCR product was digested with NotI and SalI while the luciferase (and HSV-tk) PCR product was digested using SalI and BamHI. The digested shuttle vector was ligated with digested pCCNJ and luciferase (or HSV-tk) to generate pE3.1-pCCNJ-luciferase (or HSV-tk)-SV40 polyA.

Generating pCMV-mda-7-pA-pE3.1: pCMV was PCR amplified from pcDNA3.1/Hygro(+) (Invitrogen) using the primers, sense: 5'-AAGGAAAAAAGCGGCCGCCGATG-TACGGG CCAGATA-3' (SEQ ID NO:7) and antisense: 5'-GTACACGCGTCGACAATTTCGATAAGC CAG-TAAGC-3' (SEQ ID NO:8); MDA-7 was PCR amplified using primers, sense: 5'-GTACACGCGTCGAC GCCGCCA TGAATTTTCAACAGAGGC-3' (SEQ ID NO:9) and antisense: 5'-ATCGCGGATCCTCAGAGCTT-GTA GAATTTC-3'(SEQ ID NO:10) and a synthetic poly A tail was generated by annealing oligos, sense: 5'-GATC-CAATAAAATATCTTTATTTTCATTACATCTGTGTGT-TGGTTTTTTGTG TGA-3'(SEQ ID NO:11) and antisense: 5'-CTAGTCACAC AAAAAACCAACACACAGATG-TAATGAAAATAAAG ATATTTTATTG-3' (SEQ ID NO:12). The E3 region specific shuttle vector pE3.1 was digested using BamHI and SpeI and ligated to the annealed synthetic poly A tail. The shuttle vector containing the poly A tail was next digested with NotI and BamHI, the pCMV PCR product was digested with NotI and SalI while the mda-7 PCR product was digested using SalI and BamHI. The digested shuttle vector was ligated with digested pCMV and mda-7 to generate pE3.1-pCMV-mda-7-synthetic polyA.

A shuttle plasmid for inserting two expression cassettes in tandem into the E3 region of the viral vector was constructed using plasmids pE3.1-CMV-mda-7 and pE3.1-CCN1-Luc (FIG. 2). Specifically, the 2803 bp XbaI-SgfI fragment from pE3-CMV-mda-7 was ligated with the 3475 bp SpeI-SgfI fragment from pE3-CCN1-Luc2, generating plasmid pE3-Luc2-mda-7.

The cosmid containing the entire sequence of the recombinant tripartite virus was constructed by ligating the 4250 bp BstAPI fragment from pE3-Luc2-mda-7 with the 1586 bp PflMI fragment from PEG-pE1.2 and SfiI-digested pAd328. pAd328 is a 39 kb plasmid that contains the sequences encompassing by 466-right end (1.3-100 mu) of the Ad5 genome, with a 2.7 kb deletion in the E3 region. The cosmid was linearized with SwaI and transfected into 293 cells in order to rescue the tripartite virus.

Also, the following controls were constructed:
1. Ad-PEG-E1A-CCN1-Luc2
2. Ad-PEG-E1A-CMV-mda-7
3. Ad-PEGE1-null Example 2

Construction of a Tripartite Cancer Theranostic Virus: Ad5.PEGE1-CMVMda7-CCN1tk (TCTV-Tk7)

A conditionally-replicative adenovirus vector containing the E1A/B (E1A/E1B) region under the control of a PEG promoter and two expression cassettes in the E3 region (CMV-mda-7 and CCN1-tk) were constructed using the AdenoQuick1.0 system (FIG. 3).

The shuttle plasmid for inserting the PEG promoter upstream of the E1a/b (E1A/E1B) coding sequences (PEG-pE1.2) and pCMV-mda-7-pA were generated as described for the earlier construct.

Generating pCCN1-HSV-1-sr39tk-SV40 pA-pE3.1: pCCNJ was PCR amplified using primers, sense: 5'-AAGGAAAAAAGCGGCCGCAAAACAAACAAGTA-CAACATAC-3' (SEQ ID NO:1) and antisense: 5'-GTA-CACGCGTCGAC GGCGCCCCGGAGCCCGCCTTT-3' (SEQ ID NO:2); HSV-1-sr39tk was PCR amplified using primers, sense 5'-GTACACGCGTCGACGCCGCCATGC-CCAC GCTACTGC-3' (SEQ ID NO:13) and antisense: 5'-ATCGCGGATCCTCAGTTAGCC TCCCCCAT-3'(SEQ ID NO:14) and SV40 poly A was PCR amplified using primers, sense: 5'-ATCGCGGATCCGAGATTTC GATTC-CACCG-3' (SEQ ID NO:5) and antisense: 5'-GGACTAGTCAGGCTTTACACTTTATGC-3' (SEQ ID NO:6). The E3 region specific shuttle vector pE3.1 and the SV40 polyA PCR product were digested using BamHI and SpeI and ligated. The shuttle vector containing the poly A tail was next digested with NotI and BamHI, the pCCN1 PCR product was digested with NotI and SalI while the HSV-1-sr39tk PCR product was digested using SalI and BamHI. The digested shuttle vector was ligated with digested pCCN1 and HSV-1-sr39tk to generate pE3.1-pCCN1-HSV-1-sr39tk-SV40 polyA.

A shuttle plasmid for inserting two expression cassettes in tandem into the E3 region of the viral vector was constructed using plasmids pE3.1-CMV-mda-7 and pE3.1-CCN1-tk (FIG. 4). Specifically, the 1866 bp BsmBI fragment and the 605 bp BsmBI-SpeI fragment from pE3.1-CMV-mda-7 was ligated with the 3658 bp XbaI-BsmBI fragment from pE3.1-CCN1-tk, generating plasmid pE3-mda-7-tk.

The cosmid containing the entire sequence of the recombinant tripartite virus was constructed by ligating the 4339 bp DraIII fragment from pE3-mda-7-tk with the 1586 bp PflMI fragment from PEG-pE1.2 and SfiI-digested pAd328. pAd328 is a 39 kb plasmid that contains the sequences encompassing by 466-right end (1.3-100 mu) of the Ad5 genome, with a 2.7 kb deletion in the E3 region. The cosmid were linearized with SwaI and transfected into 293 cells in order to rescue the tripartite virus.

Also, the following controls were constructed:
1. Ad-PEG-E1A-CCN1-tk
2. Ad-PEG-E1A-CMV-mda-7
3. Ad-PEG-E1A Example 3

Validating the Therapeutic Efficacy of the Tripartite Virus

Therapeutic efficacy of the tripartite (Ad.PEG-E1A-CCN1-Luc2-CMV-mda-7) (TCTV-Luc7) virus was evaluated in the transgenic MMTV-PyMT (Mouse mammary tumor virus—polyoma middle T) mouse model. In order to evaluate the role of the TCTV-Luc7 virus in the MMTV-PyMT mouse model, the following two groups were evaluated—control uninjected mice and TCTV-Luc7 virus treated mice. The experimental protocol for mouse injections was as follows: $1 \times 10^8$ IU of the TCTV-Luc7 virus was injected intratumorally once visible/palpable tumors were observed. Since the MMTV-PyMT mice develop tumors at several mammary glands, the experiment was set up so as to inject at least 50% of the tumors observed (1 tumor was injected in mice with 1 or 2 tumors; 2 tumors were injected in mice showing 3 or 4 tumors and so on).

Images of the mice and tumors at the end of the experiment are shown in FIG. 5A. Injection with TCTV-Luc7 virus caused a significant reduction in tumor size as compared to those observed in control untreated mice (FIG. 5B). At sacrifice, the tumor weight of treated mice was also significantly less than tumor weights of untreated control mice. Adjacent mammary tumors in some of the untreated mice were found to be merged into a single larger tumor upon evaluation following sacrifice. A more robust effect of TCTV-Luc7 virus might be obtained by treating every single tumor that develops in the MMTV-PyMT mice.

Figure 7A:
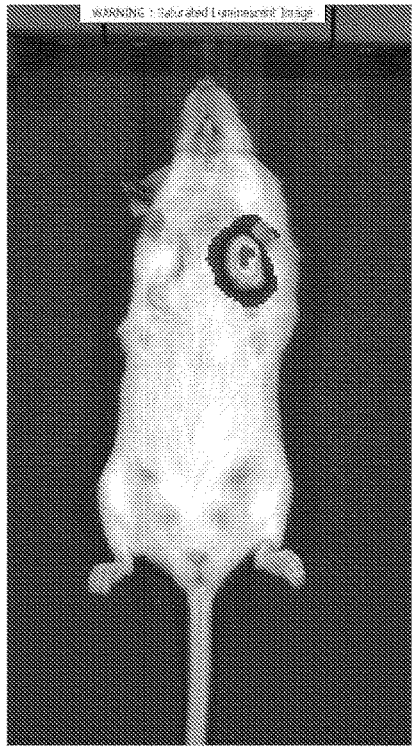
Figure 7A:
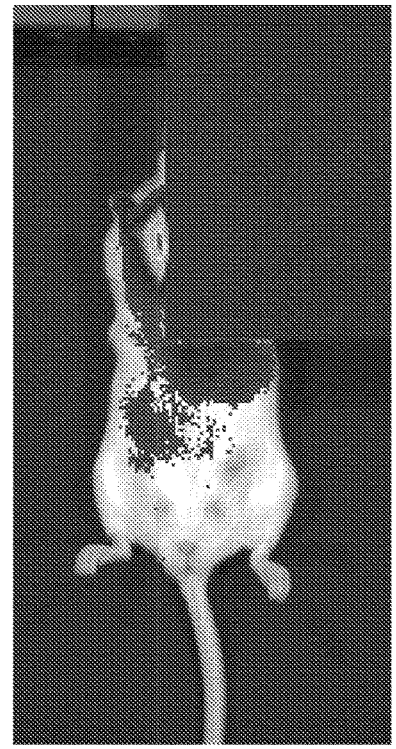
Figure 7B:
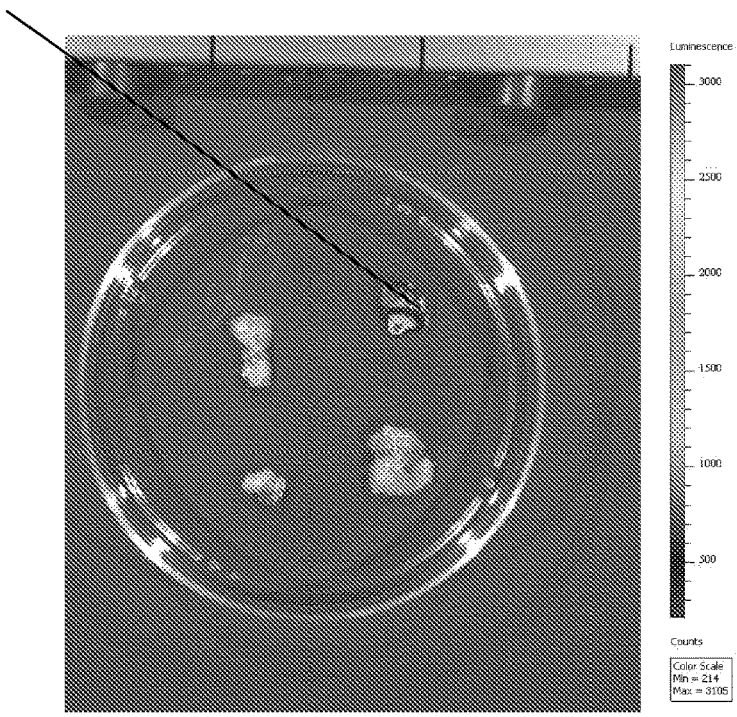
Figure 7B:
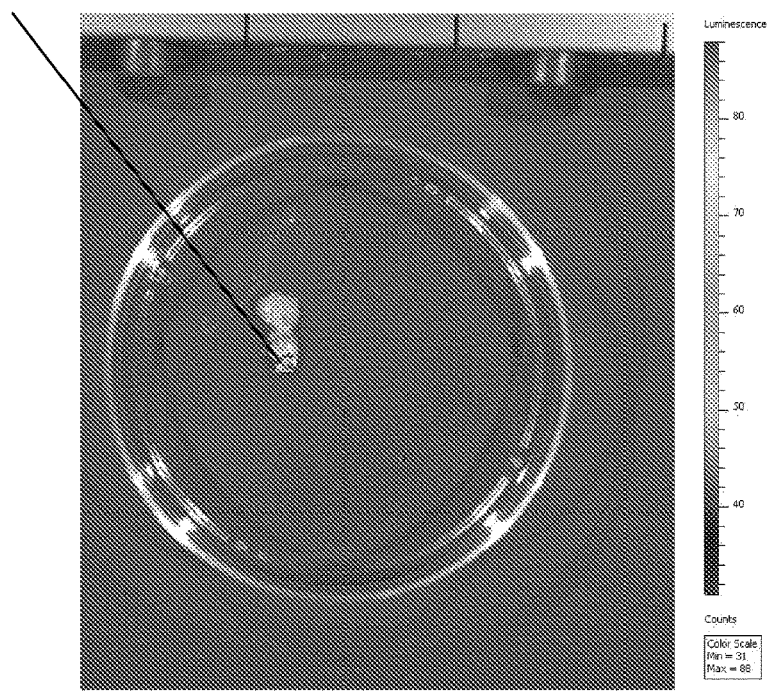

Visualizing tumors using the TCTV-Luc7 virus: Each tumor on the MMTV-PyMT mouse that is injected with the TCTV-Luc7 virus can be visualized following injection with D-luciferin by bioluminescent imaging (BLI) 24 to 48 hours post-viral injection. We wanted to determine whether injecting a single tumor with the TCTV-Luc7 virus would allow visualization of distant tumors in an MMTV-PyMT mouse. Since the luciferase signal obtained from the injected tumor is very bright (reaching saturation limits within seconds), the injected tumor was covered and the mouse was imaged using BLI. One other tumor could be visualized using this technique 24 hours after TCTV-Luc7 administration (FIG. 7A). As expected, the signal in the uninjected tumor was not as bright as that of the injected tumor (FIG. 7B).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A composition comprising a population of ultrasound targeted microbubbles, wherein the microbubbles comprise a lipid layer that stably binds a tripartite nucleic acid construct, and wherein the tripartite nucleic acid construct comprises a first promoter operably linked to at least one gene required for viral replication, a second promoter operably linked to a reporter gene, and a third promoter operably linked to a therapeutic gene, wherein the first promoter and the second promoter are each cancer-selective, and wherein the second promoter is SEQ. ID. NO. 15.

2. The composition of claim 1, wherein the nucleic acid construct is selected from the group consisting of adenoviral, lentiviral, retroviral, adeno-associated viral, and herpes simplex viral.

3. The composition of claim 2, wherein the nucleic acid construct is an adenoviral vector.

4. The composition of claim 1, wherein the first promoter is a progression-elevated gene-3 promoter (PEG-Prom).

5. The composition of claim 1, wherein the at least one gene required for viral replication is adenovirus early region IA (E1A) or early region 1B (E1B).

6. The composition of claim 1, further comprising an imaging agent selected from the group consisting of (β-galactosidase, luciferase, horse radish peroxidase, thymidine kinase, and alkaline phosphatase.

7. The composition of claim 6, wherein the imaging agent is herpes simplex virus thymidine kinase (HSV-tk).

8. The composition of claim 1, wherein the third promoter is a constitutive promoter.

9. The composition of claim 8, wherein the third promoter is cytomegalovirus (CMV) promoter.

10. The composition of claim 1, wherein the third promoter is a cancer-selective promoter.

11. The composition of claim 1, wherein the therapeutic agent is selected from the group consisting of an anti-cancer agent, an apoptosis inducing agent, a tumor suppressor agent, an immune system enhancing agent, and an immunomodulatory agent.

12. The composition of claim 1, wherein the therapeutic agent is an immunomodulatory cytokine.

13. The composition of claim 12, wherein the immunomodulatory cytokine is mda-7/IL-24.

14. The composition of claim 12, wherein the immunomodulatory cytokine is M4.

15. A composition comprising a population of ultrasound targeted microbubbles, wherein the microbubbles comprise a lipid layer that stably binds a tripartite nucleic acid construct, and wherein the tripartite nucleic acid construct comprises a first promoter operably linked to at least one gene required for viral replication, a second promoter operably linked to a reporter gene, and a third promoter operably linked to a therapeutic gene, wherein:
  (a) the first promoter is a progression-elevated gene-3 promoter (PEG-Prom);
  (b) the at least one gene required for viral replication is adenovirus early region IA (E1A) or early region 1B (E1B);
  (c) the second promoter is SEQ. ID. NO. 15;
  (d) the third promoter is cytomegalovirus (CMV) promoter; and
  (e) the therapeutic gene is an immunomodulatory cytokine selected from the group consisting of mda-7/IL-24 and M4.

16. The composition of claim 15, further comprising an imaging agent selected from the group consisting of β-galactosidase, luciferase, horse radish peroxidase, thymidine kinase, and alkaline phosphatase.

17. The composition of claim 16, wherein the imaging agent is herpes simplex virus thymidine kinase (HSV-tk).

* * * * *